United States Patent [19]

Devon

[11] Patent Number: 5,138,101
[45] Date of Patent: Aug. 11, 1992

[54] RECOVERY OF HIGH-BOILING ALDEHYDES FROM RHODIUM-CATALYZED HYDROFORMYLATION PROCESSES

[75] Inventor: Thomas J. Devon, Longview, Tex.

[73] Assignee: Eastman Kodak Company, Rochester, N.Y.

[21] Appl. No.: 732,898

[22] Filed: Jul. 19, 1991

[51] Int. Cl.$^5$ .......................... C07C 45/78; C07C 45/80
[52] U.S. Cl. ........................................ 568/492; 568/454
[58] Field of Search ........................ 568/492, 454, 451

[56] References Cited

U.S. PATENT DOCUMENTS

| | | | |
|---|---|---|---|
| 3,896,047 | 7/1975 | Aycock et al. | 568/454 |
| 4,678,857 | 7/1987 | Dureanleau et al. | 568/454 |
| 4,845,306 | 7/1989 | Puckette | 568/454 |

FOREIGN PATENT DOCUMENTS

| | | | |
|---|---|---|---|
| 0350922 | 1/1990 | European Pat. Off. | 568/492 |
| 1093346 | 10/1958 | Fed. Rep. of Germany | 568/492 |
| 1238751 | 10/1986 | Japan | 568/492 |

*Primary Examiner*—Werren B. Lone
*Attorney, Agent, or Firm*—J. Frederick Thomsen; William P. Heath, Jr.

[57] ABSTRACT

Disclosed is an extraction process for the recovery of high-boiling aldehydes produced by the rhodium-catalyzed hydroformylation of olefins in the presence of a hydroformylation solvent. The extraction process involves intimately contacting a hydroformylation product solution comprising (i) a high-boiling aldehyde, (ii) hydroformylation catalyst components comprising rhodium and an organophosphine compound, and (iii) a hydroformylation solvent with an extraction solution comprising a primary alkanol and water to form a 2-phase mixture. The phases are separated to obtain a hydroformylation solvent phase containing catalyst components and an alkanol/water phase containing the high-boiling aldehyde.

23 Claims, No Drawings

RECOVERY OF HIGH-BOILING ALDEHYDES FROM RHODIUM-CATALYZED HYDROFORMYLATION PROCESSES

This invention pertains to the recovery of high boiling aldehydes produced by the rhodium-catalyzed hydroformylation of olefins in the presence of a hydroformylation solvent. More specifically, this invention pertains to the recovery of an aldehyde from a solution comprising a rhodium catalyst, the aldehyde and a hydroformylation solvent obtained from liquid product take-off, hydroformylation processes.

The hydroformylation reaction is well-known in the art as a catalytic method for the conversion of an olefin into an aldehyde product having one carbon more than the starting mono-olefin by the addition of one molecule each of hydrogen and carbon monoxide to the carbon-carbon double bond. If the organic substrate contains more than one carbon-carbon double bond, more than one formyl group can be added to the substrate, thereby increasing the number of carbon atoms contained in the product molecule by more than one. As a result, both the molecular weight and the boiling point of the aldehyde produced increases significantly.

Most commercial hydroformylation facilities employ catalyst systems comprising rhodium and organophosphine compounds such as tertiary (trisubstituted), mono- and bis-phosphines. For example, U.S. Pat. No. 3,527,809 discloses the hydroformylation of olefins employing a catalyst system comprising rhodium and organophosphorus compounds such as triphenylphosphine (TPP) and reactor pressures below 500 psig. Hydroformylation processes which employ catalyst systems comprising rhodium in combination with other organophosphine compounds and are operated at low to moderate reactor pressures are described in U.S. Pat. No. 3,239,566 (tri-n-butylphosphine) and U.S. Pat. No. 4,873,213 (tribenzylphosphine). These catalyst systems are a great improvement over the old cobalt technology, but present certain problems when used in liquid take-off, hydroformylation processes, i.e., when the aldehyde products must be separated from mixtures of the aldehyde and the components of the catalyst system. Many of these catalyst systems are sensitive to high temperatures as is disclosed in U.S. Pat. No. 4,277,627 and other literature pertaining to catalyst systems comprising rhodium and triphenylphosphine.

The most extensive use of hydroformylation processes is in the hydroformylation of ethylene and propylene to produce propionaldehyde and isomeric butyraldehydes. These low-boiling aldehydes may be recovered by means of a gas stripped reactor wherein unreacted gases are used to sweep the aldehyde product as a vapor from the high-boiling reaction mixture contained in the reactor. Such a vapor take-off process is disclosed in U.S. Pat. No. 4,287,369. This method works well for relatively low boiling aldehyde products because of their relatively high vapor pressure at the temperature at which the hydroformylation process is operated. The method becomes progressively more impractical as the boiling point of aldehyde products increases which requires a substantial increase in the volume of the stripping gas flow in order to remove an equivalent amount of product.

Another traditional product separation technique involves the distillation of the aldehyde product from a high-boiling residue or "heel" containing the catalyst system. For example, U.S. Pat. No. 4,137,240 describes the hydroformylation of cyclic acetals of acrolein using a catalyst system comprising rhodium and triphenylphosphite. The high-boiling products of the disclosed process were separated from the catalyst heel by high-temperature, vacuum distillation, resulting in the formation of metallic rhodium which is especially undesirable since the extremely valuable metallic rhodium can plate out on the surface of the process equipment and be lost from the hydroformylation process.

U.S. Pat. No. 4,533,757 discloses a variation of the above-described vapor stripping relative to the recovery of a high-boiling aldehyde, nonanal, from a hydroformylation mixture containing rhodium and triphenylphosphine. According to this patent, a liquid reactor effluent comprising a solution of nonanal, catalyst components and a high-boiling solvent is fed to a low pressure, let-down tank. In this tank, stripping gas from the reactor is sparged up through the catalyst solution to vaporize the aldehyde product and strip it out at the lower pressure. The lower pressure requires less stripping gas than would be required if attempted at the higher pressure within the hydroformylation reactor. This method requires the use of significant amounts energy in the form of recompression of the low pressure stripping gas for recycle to the reactor. Furthermore, this method would require unacceptably high gas stripping rates for higher boiling aldehyde products such as 1,10-decanedial.

The preparation of high-boiling aldehydes, e.g., mono-aldehydes of higher molecular weights, dialdehydes and aldehydes containing other functional groups, by hydroformylation processes has been described extensively in the literature. These aldehydes may be converted to chemicals, e.g., diols, triols and diacids, useful in the manufacture of plasticizers, polyesters and polyurethanes. For example, British Patent 1,170,226 describes the stepwise hydroformylation of dicyclopentadiene and subsequent reduction of the di-aldehyde product into a mixture of tricyclic dimethanol derivatives in the same reactor. British Pat. 1,390,687 discloses the rhodium-catalyzed hydroformylation of 5-vinylnorbornene and the isolation of the di-aldehyde product by a high-temperature, vacuum distillation of the catalyst heel. Such conditions normally cause the precipitation of rhodium from the catalyst solution. German Offen. 2,226,212 describes the isolation of an analogous high-boiling aldehyde product derived from the rhodium-catalyzed hydroformylation of 8-hydroxyoctene-1 in a similar vacuum distillation procedure.

A number of references describe the preparation of high-boiling aldehydes by the hydroformylation of dienes, polyenes and olefins containing functional groups in the presence of a catalyst system comprising rhodium and an organophosphorus compound but do not provide any procedure for the separation of high-boiling aldehydes from a mixture containing the catalyst components. The hydroformylation of diolefins in the presence of a rhodium/trialkylphosphine catalyst system is disclosed in a general statement in U.S. Pat. No. 3,965,192. U.S. Pat. Nos. 3,499,932 and 3,499,933 disclose the stepwise hydroformylation of dicyclopentadiene to a di-aldehyde using rhodium/triphenylphosphine and rhodium triphenylphosphite catalyst systems. U.S. Pat. No. 3,787,459 discloses the hydroformylation of methyl esters of linoleic acid using a rhodium on carbon supported catalyst. The hydroformylation of linoleyl alcohol in the presence of a rhodium/triphenylphosphine or rhodium/triphenylphosphite catalyst is disclosed U.S. Pat. No. 4,216,343. Rhodium/carbon catalyst is disclosed in the hydroformylation of 1,4- and 1,7-octadiene in the presence of a rhodium on carbon catalyst is disclosed in U.S. Pat. No. 3,557,219. The hydroformylation of dienes and polyenes using rhodium/trialkylphosphine catalysts is disclosed in general in U.S. Pat. No. 3,239,566.

The following patents refer to the use of distillation procedures in the isolation high-boiling aldehydes produced by the hydroformylation of olefins containing a functional group: U.S. Pat. No. 2,894,038 hydroformylation of 4-formylcyclohexene using a rhodium/cobalt catalyst; U.S. Pat. No. 3,966,827 hydroformylation of 4-hydroxy-2-methylbutene-1; U.S. Pat. No. 4,275,243—recovery of 4-hydroxybutyraldehyde. It is evident from the numerous and varied types of aldehydes mentioned that there is a need for a method of product separation that does not employ the high temperatures that are required to isolate the high-boiling aldehydes by conventional distillation techniques.

A number of different techniques for separating hydroformylation catalysts from aldehydes have been described in the literature. U.S. Pat. Nos. 4,144,191 and 4,262,147 describe the use of specific mixed rhodium/-cobalt carbonyl cluster catalysts bound to amine groups on a polymer support. This catalyst was specifically designed for the "one pot" sequential hydroformylation and reduction steps using dicyclopentadiene for conversion into tricyclic dimethanol product. U.S. Pat. No. 4,533,757 discloses that this system looses rhodium from the resin support to the oxo product.

Another approach which has been disclosed in the literature is the use of functionalized, water-soluble, organophosphorus compounds in combination with rhodium. U.S. Pat. No. 3,857,895 discloses the use of aminoalkyl and aminoaryl organophosphine compounds in combination with rhodium. The catalyst solution containing the aldehyde product is extracted with aqueous acid to recover the rhodium and organophosphine catalyst components from an aldehyde-containing, organic solution. Since the acid must be neutralized to recover the catalyst in a form that can be readmitted to the reactor, the process presents salt disposal problems.

The use of polysulfonated triarylphosphines has been disclosed in a number of patents. U.S. Pat. No. 4,399,312 describes the use of catalyst systems comprising rhodium and alkali metal salts of triarylphosphines substituted with sulfonic acid or carboxylate groups as hydroformylation catalysts. The reactor effluent of these systems is treated with water to remove the rhodium phosphine complex from the organic solution containing the aldehyde product. The process of U.S. Pat. No. 4,248,802 uses a similar tri-sodium salt of a trisulfonated-triphenylphosphine compound in a two-phase water-/organic solvent mixture in the hydroformylation reactor. The rhodium and phosphine components of the catalyst are recovered in the aqueous phase by separating the phases after the mixture leaves the reactor and is cooled. This method is most suitable in the hydroformylation of relatively water-soluble aldehyde products which promote a homogeneous mixing of the two phases at the high temperatures in the reactor. The method is less successful when used with higher olefins that are less soluble in water and do not dissolve as effectively into the aqueous phase containing the catalyst in the reactor under hydroformylation conditions.

The use of aqueous solutions containing 2-N,N-dimethylaminoethanol in the treatment of catalyst solutions containing rhodium carbonyl is disclosed in U.S. Pat. No. 4,292,196. According to the patent, 70 percent of the rhodium is extracted into the aqueous phase.

Other phase separation methods have been disclosed in the literature for use in conjunction with certain specific hydroformylation processes. U.S. Pat. No. 2,850,536 discloses that when dicyclopentadiene is hydroformylated in heptane using cobalt carbonyl catalyst, the dialdehyde product separates from the heptane in a separate phase. It was noted that most of the cobalt catalyst also was contained in this product layer.

There are many patents pertaining to the hydroformylation of allyl alcohol wherein an aqueous extraction has been employed to separate the 4-hydroxybutyraldehyde product from the solution containing the catalyst. This special case reflects the substantial water solubility of both the allyl alcohol feedstock and product 4-hydroxybutyraldehyde. Thus, as disclosed in U.S. Pat. No. 4,215,077, it is important that very high conversions of allyl alcohol, preferably above 95 percent, are achieved in the hydroformylation reactor. Another aspect of this specific technology (manufacture of 4-hydroxybutyraldehyde) is the problem of separating the rhodium catalyst from the aqueous extract of 4-hydroxybutyraldehyde. In practice, the aqueous extract is limited to about 10 percent 4-hydroxybutyraldehyde to suppress the loss of rhodium to the aqueous phase as is noted in U.S. Pat. No. 4,567,305 wherein the catalyst system consisted of rhodium and triphenylphosphine. U.S. Pat. No. 4,678,857 discloses that 5 mg of rhodium per liter of aqueous phase was extracted into the aqueous phase when the 4-hydroxybutyraldehyde concentration was 38 percent by weight.

A problem inherent in the described extraction procedure is the separation of the rhodium-containing, organic phase from the 4-hydroxybutyraldehyde-containing aqueous extract. U.S. Pat. No. 4,678,857 proposes that this problem may be overcome by the use of halogenated aromatic compounds to increase the density differences between the organic layer and the aqueous layer. Brominated aromatic compounds are, in general, undesirable from the standpoint of toxicity and as potential catalyst poisons. The use of the aqueous extracts of 4-hydroxybutyraldehyde as feedstocks for catalytic hydrogenation to 1,4-butanediol is disclosed in U.S. Pat. Nos. 4,083,882 and 4,064,145. Once again, the relatively low concentration of 4-hydroxybutyraldehyde in the aqueous solution used in the hydrogenation requires a large amount of energy to remove the water from the dilute 1,4-butanediol product.

The use of alcohols as a solvent in the reactor of hydroformylation processes has been disclosed in a number of patents. In most of the examples wherein a particularly desirable effect is demonstrated, the effect is due to the conversion of some of the more sensitive aldehyde products into acetal derivatives by the reaction of two moles of alcohol with one mole of aldehyde functional group to form one mole of acetal and one mole of water. The conditions favoring the reaction are low concentrations of water in the reactor and high reactor temperatures to complete the reaction. U.S. Pat. No. 2,880,241 discloses the use of an alcohol solvent in the rhodium carbonyl-catalyzed hydroformylation of dicyclopentadiene whereby the effective yield to the dialdehyde products is increased by their conversion to more stable diacetal derivatives under the high temperatures used in the hydroformylation.

U.S. Pat. No. 4,101,588 discloses the use of alcohol and diol solvents in the hydroformylation of the conjugated diene 1,3-butadiene in the presence of (TPP)$_2$Rh(CO)Cl catalyst (TPP=triphenylphosphine). The conversion of the intermediate penteneal to the corresponding acetal greatly suppressed the side reaction of the reduction of this material to normal pentanal. The use of the halogen containing catalyst precursor apparently is important for the success of this process by forming an acid which is required to promote the formation of the acetal. U.S. Pat. No. 4,507,508 describes the addition of an acid to the reactor in 1,3-butadiene hydroformylation in alcohol solvent to increase the yield of the acetal products. One of the catalysts used in this latter patent was triphenylphosphite, a ligand that is sensitive to acid hydrolysis as disclosed in U.S. Pat. No. 4,789,753.

U.S. Pat. No. 4,742,178 discloses the use of methanol as a reactor solvent in the hydroformylation of 1,7-octadiene in the presence of a catalyst system comprising rhodium and a bidentate diorganophosphine ligand, i.e., a bis-tertiary phosphine compound, that is very selective to the formation of linear aldehyde product. The product solution containing the catalyst components and acetal product then was treated with a nickel hydrogenation catalyst and hydrogen to reduce the diacetal to 1,10-decanediol product. The procedure did not consider the separation of the expensive rhodium phosphine catalyst components from the product and, in the example cited, the catalyst system was sacrificed during the hydrogenation step.

The state of the art provided hereinabove establishes a need for a means for separating high-boiling aldehyde products from hydroformylation catalyst systems comprising rhodium and organophosphine compounds without the use of high temperatures that are normally required for distillation or gas stripping techniques of product separation. Such separation means must be adaptable to continuous operation wherein the catalyst components can be separated efficiently from the aldehyde products and returned to the hydroformylation reactor zone. The separation means also should provide the high-boiling aldehyde products in a form suitable for further processing such as in processes whereby the aldehydes are converted to alcohol, carboxylic acid or amino derivatives.

I have discovered that high-boiling aldehydes may be separated from hydroformylation solutions comprising a high-boiling aldehyde, catalyst components comprising rhodium and an organophosphine compound, and a hydroformylation solvent by intimately contacting (extracting) the mixture with a solution comprising a primary alkanol and water. The extraction mixture comprising the hydroformylation and alkanol/water solutions is allowed to separate into 2 phases: a hydroformylation solvent phase containing the catalyst components and an alkanol/water phase containing the aldehyde. The hydroformylation solvent phase may be returned to the hydroformylation reactor and the aldehyde-containing alkanol/water phase may be processed further, either to recover the aldehyde or to convert the aldehyde to other compounds.

The process of the present invention therefore provides a means for the recovery of an aldehyde product from a hydroformylation product solution comprising (i) a high-boiling aldehyde, (ii) hydroformylation catalyst components comprising rhodium and an organophosphine compound, and (iii) a hydroformylation solvent by the steps of:

(1) intimately contacting the hydroformylation product solution with an extraction solution comprising a primary alkanol and water to form a 2-phase mixture;

(2) separating the mixture of step (1) to obtain:
   (a) hydroformylation solvent phase containing catalyst components; and
   (b) an alkanol/water phase containing the high-boiling aldehyde.

The process may be employed for the recovery of aldehydes which have a boiling point greater than about 100° C. (at atmospheric pressure) and thus cannot be easily removed as a vapor from the hydroformylation reactor. The process may be operated in a manner whereby essentially none of the catalyst system components, e.g., a catalytically-active, complex rhodium-phosphine compound and additional or excess phosphine, is extracted by the alkanol/water solution. Thus, operation of the recovery process does not result in any significant loss of catalyst from the hydroformylation production system since the hydroformylation solvent phase containing the catalyst components may be recycled to the hydroformylation reactor. The aldehyde-containing alkanol/phase may be used as the feed to known hydrogenation or oxidation processes wherein the aldehyde is converted to an alkanol or carboxylic acid. Alternatively, the aldehyde may be isolated by the removal of the water and alkanol by distillation under reduced pressure.

The hydroformylation product mixture employed in the present invention may be provided by the many hydroformylation processes described in the literature, including the patents referred to hereinabove, wherein an olefin is contacted with a mixture of carbon monoxide and hydrogen in the presence of a hydroformylation solvent and a catalyst system comprising rhodium and a tertiary phosphine compound under hydroformylation conditions of temperature and pressure. Typically, the rhodium concentration in the hydroformylation product solution is about 1 to 5000 ppm and the concentration of the tertiary phosphine compound gives a ratio of moles phosphine to gram atom rhodium of at least 1:1, more commonly from about 5:1 to 100:1.

The aldehydes which may be recovered or separated in accordance with the present invention comprise aliphatic, including aliphatic aldehydes derived from ethylenically-unsaturated, low molecular weight polymers, alicyclic, aromatic and heterocyclic compounds containing one, two, three or more aldehyde (formyl or carboxaldehyde) groups. The aldehydes may contain up to about 40 carbon atoms and have a boiling point (at atmospheric pressure) of at least 100° C. and more typically at least 125° C.

Examples of the aliphatic, mono aldehydes which may be utilized in the process include unsubstituted and substituted, aliphatic mono aldehydes containing up to about 20 carbon atoms. Examples of the groups which may be present on the substituted aldehydes include hydroxy; alkoxy including ethers and acetals; alkanoyloxy such as acetoxy; amino including substituted amino; carboxy; alkoxycarbonyl; carboxamido; keto; and the like. Preferred aliphatic mono aldehydes have the general formulas:

wherein
R¹ is straight- or branched-chain alkyl of about 5 to 8 carbon atoms;
R² is straight- or branched-chain alkylene having about 2 to 18 carbon atoms; and
R³ is hydroxy, alkoxy of up to about 4 carbon atoms, alkanoyloxy of up to about 4 carbon atoms, carboxyl or alkoxycarbonyl of 2 to about 10 carbon atoms.

Specific examples of the aliphatic mono-aldehydes include 4-hydroxybutyraldehyde, 4-acetoxybutyraldehyde and 4-hydroxy-2-methylbutyraldehyde.

The aliphatic, di-aldehydes may contain up to about 40 carbon atoms. Preferred aliphatic, di-aldehydes have the general formula:

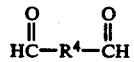

wherein R⁴ is straight- or branched-chain alkylene having about 5 to 20 carbon atoms.

The cyclic aldehydes which may be used in the separation process of the present invention may be derived according to known processes from cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic aldehydes include 4-(2-formylethyl)cyclohexanecarboxaldehyde, 1,4-cyclohexanedicarboxaldehyde, 4-formylcyclohexanecarboxylic acid, methyl 4-formylcyclohexanedicarboxylate, 1,4-cyclooctanedicarboxaldehyde, 1,5,9-cyclododecanetricarboxaldehyde, 2-(5,5-dimethyl-1,3-dioxanyl)acetaldehyde, 2-(formylnorbornanyl)acetaldehyde and 3-phenylpropionaldheyde. A preferred group of cyclic aldehydes comprise cycloaliphatic aldehydes having the general formula:

wherein
R⁵ is cycloalkylene having about 5 to 12 carbon atoms; and
R⁶ is formyl, formylethyl, carboxyl or alkoxycarbonyl of 2 to about 10 carbon atoms.

The aldehyde or aldehydes which are separated in accordance with the present invention may constitute about 1 to 80 weight percent of the total weight of the hydroformylation product solution depending, for example, on the particular aldehyde or aldehydes produced by the hydroformylation production system and the hydroformylation solvent and conditions employed. However, aldehyde concentrations of about 10 to 50 weight percent (same basis) are more common.

As mentioned hereinabove, the hydroformylation product solution employed in the present invention comprises, in addition to at least one of the above-described aldehydes, a catalyst system comprising rhodium and an organophosphine compound, and a hydroformylation solvent. Examples of the organophosphine component of the catalyst system are described in the patents referred to herein, including the references cited therein. Additional organophosphines are disclosed in U.S. Pat. Nos. 4,742,178, 4,755,624, 4,774,362 and 4,873,213. The organophosphine compounds typically are mono- and bis-tertiary (trisubstituted) phosphines having the general formulas:

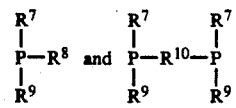

wherein R⁷, R⁸ and P⁹ are the same or different and each is hydrocarbyl containing up to about 12 carbon atoms and R¹⁰ is a hydrocarbylene group which links the 2 phosphorus atoms through a chain of 2 to 22 carbon atoms. Examples of the groups represented by R⁷, R⁸ and R⁹ include alkyl including aryl substituted alkyl such as benzyl, cycloalkyl such as cyclohexyl, and aryl such as phenyl and phenyl substituted with one or more alkyl groups. Alkylene of 2 to 8 carbon atoms, cyclohexylene, phenylene, naphthylene and biphenylene are examples of the hydrocarbylene groups which R¹⁰ may represent.

The preferred organophosphorus ligands are those which exhibit limited solubility in the extraction solvent and are not reactive with water or the primary alcohols used in the extraction solvent. Preferred tertiary phosphine compounds include tri-alkylphosphine ligands such as tri-n-butylphosphine, tri-n-octylphosphine, tribenzylphosphine, tricyclohexylphosphine, dicyclohexyl-n-octylphosphine; triarylphosphines such as triphenylphosphine, tri-o-tolylphosphine, tri-p-tolylphosphine, trinapthylphosphine; and mixed aryl-alkylphosphine compounds such as dicyclohexylphenylphosphine, cyclohexyldiphenyl-phosphine, diphenyl-n-hexylphosphine. Chelating bidentate phosphines such as the ligand, α,α'-bis(diphenylphosphino)-o-xylene, 2,2'-bis(diphenylphosphinomethyl)-1,1'-biphenyl (BISBI), trans-1,2-bis(diphenylphosphinomethyl)cyclobutane, 1,4-bis(diphenylphosphino)butane, and 1,2-bis(diphenylphosphino)ethane are also examples of suitable tertiary phosphine compounds. The preferred organophosphine compounds do not have polar functionality that increase their solubility in the aqueous alcohol extraction solvent. Triorganophosphite ligands such as triphenylphosphite and the analogous bidentate derivatives are suitable for use in this invention although these organophosphorous compounds are not as stable as triorganophosphine compounds when exposed to water or alcohol.

The solvent component of the hydroformylation product solution may be selected from various alkanes, cycloalkanes, alkenes, cycloalkenes and carbocyclic aromatic compound which are liquids at standard temperature and pressure and have a density which is at least 0.02 g/mL different from the density of the extraction solvent employed. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; and alkenes and cycloalkenes such as 1,7-octadiene, dicyclopentadiene, 1,5-cyclooctadiene, octene-1, octene-2, 4-vinylcyclohexene, cyclohexene, 1,5,9-cyclododecatriene, pentene-1 and crude hydrocarbon mixtures such as naphtha and kerosene. Generally, solvents having polar functional groups, e.g., ketones and esters, or atoms other than carbon and hydrogen are not preferred because such solvents do not possess satisfactory partitioning characteristics and/or adversely affect the catalyst system. However, certain polar compounds such as dialkyl benzenedicarboxylate esters, e.g., bis(2-ethylhexyl) phthalate, have been found to give good results. It will be apparent to those skilled in the art that the particular aldehyde produced in the hydroformylation production system may exclude the use of certain solvents. The hydroformylation solvent preferably has a density which is at least 0.05 g/mL different from the density of the extraction solvent employed. For certain hydroformylation solvents, the use of extraction solutions consisting of specific alkanol:water ratios is required to achieve satisfactory phase separation.

The preferred hydroformylation solvents are alkanes having about 5 to 20 carbon atoms, alkyl substituted benzenes having about 9 to 15 carbon atoms, tetrahydronaphthalene, and decahydronaphthalene.

In accordance with the first step of the extraction process of the present invention, the hydroformylation product solution described above is intimately contacted with an extraction solvent comprising a primary alkanol and water. The use of primary alkanols having up to 3 carbon atoms, especially methanol and ethanol, provide the best results. In the operation of the extraction process, the primary alkanol may convert the aldehyde to be recovered to an equilibrium mixture of the aldehyde and its hemiacetal. Such hemiacetals are believed to be more polar than the aldehyde precursors and are more soluble in the extraction solvent. Thus, in specifying that the aldehyde is recovered in the alkanol/water phase according to my novel process, it is to be understood that the term "aldehyde" includes hemiacetals thereof.

The relative amounts of alkanol and water constituting the extraction solution can vary substantially depending, for example, on the particular aldehyde to be recovered and the hydroformylation solvent employed. Generally, as the ratio of carbon atoms to aldehyde (formyl) groups, or the ratio of carbon atoms to aldehyde groups, of the aldehyde increases, the ratio of alkanol to water should be increased to maximize extraction efficiency. However, the extraction solvent must contain sufficient water to allow the separation of the hydroformylation solvent and the extraction solution into 2 phases. The alkanol:water volume ratio normally is in the range of about 20:1 to 1:20, preferably about 5:1 to 1:1.

The partitioning of the aldehyde products between the hydroformylation solvent and the alkanol/water extraction solution is an equilibration process. The relative volumes of extraction solution and hydroformylation product solution is determined by the solubility of the various aldehyde products in the particular combination of solutions being utilized, the alkanol content of the alkanol/water extraction solution, and how much aldehyde product is to be removed. For example, if the aldehyde to be separated has a high solubility in the extraction solvent and is present in the hydroformylation product solution in a relatively low concentration, a low volume ratio of extraction solution to hydroformylation product solution may be used to effect practical extraction of the product. Larger concentrations of the product normally require the use of a higher extraction solution:hydroformylation product solution volume ratio to achieve a practical degree of extraction of the product aldehyde from the hydroformylation product solution. When the aldehyde product has a low relative solubility in the extraction solution, more extraction solution per unit volume of hydroformylation product solution is required. The volume ratio of extraction solution:hydroformylation product solution therefore may vary from about 10:1 to 1:10. However, by the judicious choice of hydroformylation solvent, alkanol and alkanol:water volume ratios, volume ratios of extraction solution:hydroformylation product solution in the range of about 1:1 to 1:4 may be used for the recovery of most aldehyde products.

I have found that the solubility of the aldehyde product in the extraction solution is higher at lower extraction temperatures. Thus, no advantage is achieved by using temperatures greater than those of the hydroformylation reaction temperature, e.g., about 70° to 125° C., and superior results are obtained when the extraction temperature is lower than that of the hydroformylation reactor. The extraction process preferably is carried out at a temperature in the range of about 20° to 60° C. The 20° to 60° C. range is the most practical from the standpoints of extraction efficiency, speed of reaching equilibration and energy considerations.

The time over which the hydroformylation product solution and extraction solution are contacted, i.e., prior to phase separation, is dependent upon the speed at which the phases reach equilibrium. In practice this may vary from a minute or less to impractically long mixing times in excess of three hours.

I also have found that the amount of rhodium extracted by the extraction solution is suppressed by the inclusion of a salt of a carboxylic acid in the extraction solution. Thus, in a second embodiment of the process of the present invention, step (1) set forth hereinabove comprises intimately contacting the hydroformylation product solution with an extraction solution comprising a primary alkanol, water and a salt of a carboxylic acid to form a 2-phase mixture. The preferred salts are alkali metal, i.e., lithium, sodium, potassium, rubidium and cesium, carboxylates. It is further preferred that the salts are alkali metal salts of carboxylic acids having 4 to 30 carbon atoms, most preferably from 8 to 18 carbon atoms.

The concentration of the carboxylate salt in the extraction solution may vary widely. The effective amount of the carboxylate salts depends, for example, on the particular carboxylate salt used, the concentration of water in the extraction solution and the particular hydroformylation catalyst system employed in the hydroformylation production system. Certain catalyst systems such as the BISBI/Rh catalyst system require relatively high concentrations of the salts to suppress extraction of rhodium by the extraction solution. Other catalyst systems such as trioctylphosphine/Rh and tricyclohexylphosphine/Rh require lower concentrations. The concentration of the carboxylate salt in the extraction solvent typically will provide an alkali metal concentration of about 1 to 5000 parts per million (1 mg to 5000 mg per liter of extraction solution). The preferred concentration of the preferred alkali metal carboxylate salts provides an alkali metal concentration of about 10 to 1400 ppm in the extraction solution.

Although the process of the present invention may be practiced as a batch process, it preferably is carried out in a continuous mode of operation in conjunction with a continuous hydroformylation production system. Thus, hydroformylation product solution and extraction solution may be fed continuously to an agitated vessel and overflowed into a liquid/liquid separation apparatus wherein the 2 phases are separated. Alternatively, the extraction and hydroformylation product solutions may be fed countercurrently to a continuous, packed column extractor. Another mode of operation employs an agitated vessel in combination with a Karr reciprocating plate extraction column wherein the extraction and hydroformylation product solutions are fed to the agitated vessel to which also is fed a mixture of the 2 solutions taken from the mid section of the extraction column. The mixture from the agitated vessel is fed to the extraction column to which also may be fed extraction solution at a point, typically at or near the top of the extraction column, to achieve a counter current flow of the extraction and hydroformylation product solutions.

The extraction process described herein is the equilibration of a particular compound dissolving into two separate liquid phases. The effectiveness of the present extraction process may be measured in terms of the partition coefficient (Kp) for a compound "X" which is defined as:

$$Kp = \frac{\text{(concentration of } X \text{ in extraction solvent)}}{\text{(concentration of } X \text{ in hydroformylation solvent)}}$$

For the process of the present invention, it is desirable to have Kp values for the high-boiling aldehyde as high as possible in partitioning the aldehyde between the hydroformylation solvent and the extraction solution. High Kp values give high extraction efficiencies requiring lower amounts of extraction solution. Similarly, it is desirable that the Kp of the hydroformylation solvent be a low value. This simplifies purification of the aldehyde products down-stream. In the hydroformylation of diolefins to dialdehydes, it also is desirable to have Kp values for the dialdehyde products larger than the Kp values of the intermediate mono-aldehyde mono-olefin (formyl-olefin) intermediate formed in the hydroformylation reaction. This permits recycling of the formyl-olefin to the hydroformylation reactor in the hydroformylation solvent for further reaction to the desired dialdehyde product, while selectively extracting the desired di-aldehyde product. Likewise, for the same reason, it is desirable to have low Kp values for the olefin or polyolefin feedstocks used in the process.

This selective extraction contrasts with a product separation scheme using conventional distillation or gas-stripping product removal from a high-boiling catalyst heel wherein the lower boiling olefin feed and formyl-olefin intermediate are removed from the catalyst prior to the isolation of the high-boiling dialdehyde products. Such olefins and formyl olefins would have to be separated from the desired aldehyde product and then recycled to the hydroformylation reactor. The extraction solvent should provide high Kp values for the desired aldehyde products while providing low Kp values for the hydrocarbon solvent and organophosphine compounds and Rh complexes thereof.

A third embodiment of the present invention involves a second extraction wherein the alkanol/water phase containing high-boiling aldehyde which is obtained with the process described hereinabove is intimately contacted with an organic solvent selected from hydroformylation solvent, olefin feedstock, i.e., the olefin from which the high-boiling aldheyde is derived, or a mixture thereof. The purpose of the second extraction is to recover in the organic solvent any catalyst components, i.e., rhodium and/or organophosphine compound, which are extracted into the alkanol/water phase in the first or primary extraction.

The organic solvent containing the catalyst components then may be recycled to the hydroformylation reactor. In production systems wherein the high-boiling aldehyde is a di- or tri-aldehyde, the second extraction also can recover in the organic phase intermediate hydroformylation products, e.g., formyl-olefin compounds, present in the alkanol/water phase. This embodiment of the present invention adds the following third and fourth steps to the two-step process defined above:

(3) intimately contacting the alkanol/water phase of step (2) with an organic solvent selected from hydroformylation solvent, olefin feedstock or a mixture thereof; and (4) separating the mixture of step (3) to obtain:
  (a) an organic solvent phase containing catalyst components present in the alkanol/water phase of step (3); and
  (b) an alkanol/water phase containing the high-boiling aldehyde.

The secondary extraction may be carried out by counter current flow techniques described above or by vigorously agitating a mixture of the organic solvent and the alkanol/water phase, using at least 0.05 volume of organic solvent per volume of the alkanol/water phase. The volume ratio of the organic solvent to the alkanol/water phase typically is in the range of about 0.2:1 to 1:1. The secondary extraction may be carried out at a temperature of about 0° to 70° C. with a range of about 10° to 30° C. being preferred.

The alkanol/water phase containing the high-boiling aldehyde may be subjected further to convert the aldehyde to its derivatives such as alcohols or carboxylic acids corresponding to the aldehyde. Alternatively, the high-boiling aldehyde may be isolated from the alkanol/water phase by the steps comprising (i) heating the alkanol/water phase containing the high-boiling aldehyde to vaporize at least 50 weight percent of the alkanol and form a separate liquid phase of the aldehyde and (ii) separating the aldehyde from the liquid phase, e.g., by centrifugation or filtration techniques. Sufficient alkanol may be removed (vaporized) from the alkanol/water phase to precipitate the aldehyde by heating the alkanol/water phase at a temperature of about 25° to 100° C. at pressures in the range of about 20 torr to ambient pressure.

Another embodiment of my novel process includes a hydrogenation step wherein the alkanol/water phase containing high-boiling aldehyde product is subjected to catalytic hydrogenation at elevated temperature and pressure to convert the aldehyde to the corresponding alcohol. This embodiment of the process may, of course, be utilized with any of the other embodiments described hereinabove and provides an additional step comprising:

subjecting the alkanol/water phase containing the high-boiling aldehyde to catalytic hydrogenation to convert the aldehyde to the corresponding alcohol.

Suitable hydrogenation catalysts include Raney nickel, Raney cobalt, molybdenum promoted nickel, copper chromite and supported Group VIII noble metals such as ruthenium on carbon, platinum on alumina, platinum on carbon and palladium on carbon. Typical hydrogenation conditions which may be used comprise temperatures of about 25° to 150° C. and total pressures of about 10 to 1000 psig with temperatures and pressures in the range of about 100° to 150° C. and 100 to 500 psig being preferred.

The following reference examples illustrate the hydroformylation of olefins using a catalyst system comprising an organophosphine compound and rhodium. The hydroformylation reactor is a vertically-mounted, stainless steel pipe 1.22 meters tall by 2.54 centimeters inside diameter (4 feet by 1 inch i.d.). The temperature of the reactor is controlled by the use of a circulating hot oil bath and is measured by a thermocouple contained in an internal well. The gas feeds of hydrogen, carbon monoxide and nitrogen are fed from high pressure cylinders using either rotameters or airactuated control valves operating off of differential pressure (D/P) cells that measure flow. The gas flows are purified using commercial "Deoxo" catalyst beds as supplied from Engelhard Industries to remove traces of oxygen from the streams. The carbon monoxide Deoxo bed is heated to 125° C. The carbon monoxide stream is also purified to remove traces of iron pentacarbonyl using a supported potassium hydroxide bed as described in U.S. Pat. No. 4,608,239. The gases are fed to and distributed in the reactor through a filter element that is welded into the side of the reactor at the bottom. Pressure is controlled by use of an air actuated control valve operating off of a pressure control box.

The reactor has a screwed plug at the top that is used for the addition of catalyst to the reactor. The bottom of the reactor is equipped with 6.35 mm o.d. (0.25-inch), high pressure Aminco tubing that is connected to a cross fitting. The cross has a drain line, a line leading to the high pressure leg of a reactor level D/P cell and a feed line for pumping in the olefinic feedstock.

REFERENCE EXAMPLE 1

A catalyst solution was prepared under a nitrogen atmosphere using 150 mL (128.3 g) of p-diisopropylbenzene (P-DIPB) solvent, 84 mg [0.3251 millimole (mmole)] of rhodium (I) acetylacetonate dicarbonyl (RhAcAc(CO)$_2$) and 0.89 g (1.618 mmole) of 2,2'-bis(diphenylphosphinomethyl)-1,1'-biphenyl (BISBI). The catalyst solution was charged to the reactor under an argon blanket and sealed. The reactor pressure was brought to 260 psig with hydrogen, carbon monoxide and nitrogen flows. The reactor temperature was brought to 95° C. The gas flow rates (STP) to the reactor are 1.14 L/minute hydrogen, 1.65 L/minute carbon monoxide and 2.17 L/minute nitrogen. The partial pressures of hydrogen and carbon monoxide in the feed to the reactor are 63 and 91 pounds per square inch absolute (psia), respectively.

1,7-Octadiene was charged to a feed tank connected to a small positive displacement feed pump that pumped the 1,7-octadiene into the reactor via the feedline connected to the cross at the bottom of the reactor. The 1,7-octadiene was pumped into the reactor at a rate of 25 mL/hour (18.7 g/hour) for two hours. The gas feed rates and the reactor temperature were maintained for an extra two hours. The reactor was then cooled and the hydroformylation product solution was drained into a bottle under argon atmosphere. The hydroformylation product solution was analyzed by gas-liquid phase chromatography (GLC) on a 30 meter DB-1 capillary column using a flame ionization detector. The analysis was carried out using the solvent as an internal GLC standard by calculation methods that are standard in the art. The hydroformylation product solution thus produced contained 0.61 g of isomeric octadiene (C8) compounds, 8.39 g of isomeric noneneal (C9-enal, monohydroformyled product) and 38.90 g of isomeric decanedialdehyde (C10-dial). The selectivity to 1,10-decanedialdehyde was 96.6 percent of the total isomeric decanedialdehyde product.

REFERENCE EXAMPLE 2

Using the procedure described in Reference Example 1, a catalyst solution was prepared using 150 mL (128.1 g) of p-diisopropylbenzene solvent, 84 mg of RhAcAc(CO)$_2$, and 0.98 g of tricyclohexylphosphine (TCHP). The catalyst was charged to the reactor under argon and sealed. The reactor was pressured to 260 psig with hydrogen and carbon monoxide and heated to 125° C. The hydrogen and carbon monoxide flows were both set at 1.65 L/minute. The H$_2$ and CO partial pressures in the feed both are 137 psia. Trans,trans,cis 1,5,9-cyclododecatriene (CDDT) was pumped into the reactor at 25 mL/hour (22.3 g/hour) for two hours. The gas flows and reactor temperature were maintained an extra two hours before the reactor was cooled and drained of the hydroformylation product solution. The solution was analyzed using GLC techniques. The hydroformylation product solution contained 2.22 g of recovered isomeric cyclic dodecatriene compounds (C12), 8.68 g of isomeric monoformyl-cyclododecadiene compounds (C13), 30.14 g of isomeric di-formyl cyclododecene compounds (C14) and 8.01 g of isomeric tri formyl cyclododecane compounds (C15).

REFERENCE EXAMPLE 3

A catalyst solution was prepared from 84 mg of RhAcAc(CO)$_2$, 0.60 g of tri-n-octylphosphine (TOP) and 150 mL of P-DIPB solvent under nitrogen and was charged to the reactor under argon and pressured to 260 psig with hydrogen and carbon monoxide. The temperature of the reactor was brought to 125° C. and the hydrogen and carbon monoxide flows were set at 1.65 L/minute each. This corresponds to 137 psia each of hydrogen and carbon monoxide in the feedgas. 4-Vinylcyclohexene (VCH) was pumped into the reactor at 25 mL/hour (20.8 g/hour) for two hours. The reactor was kept at 125° C. and at the above gas flow rates before cooling and draining the hydroformylation product solution. The mixture was analyzed using GLC. The hydroformylation product solution contained 0.59 g of isomeric cyclic eight carbon dienes (CC8), 36.82 g of mono formyl derivatives of VCH (VCH-enal) and 15.72 g of isomeric di-formyl derivatives of VCH (VCH-dial).

REFERENCE EXAMPLE 4

A catalyst solution was prepared from 84 mg of RhAcAc(CO)$_2$, 0.29 g of tricyclohexylphosphine (TCHP) and 150 ml of p diisopropylbenzene solvent under nitrogen and was charged to the reactor under argon and pressured to 260 psig with hydrogen and carbon monoxide and heated to 95° C. The hydrogen and carbon monoxide feed rates were 5.00 L/minute and 1.00 L/minute, respectively. This corresponds to a hydrogen partial pressure in the feed of 229 psia and a carbon monoxide partial pressure of 46 psia in the feed to the reactor. Dicyclopentadiene (DCPD) was pumped into the reactor at 25 mL/hour (26.78 g/hour) over two hours. After the DCPD addition was stopped, the reactor was brought to and kept at 125° C. and at the above gas flow rates for 2 hours before cooling and draining the hydroformylation product solution which was analyzed using GLC methods. The solution contained 1.61 g of recovered DCPD, 28.57 g of isomeric mono-formyl derivatives of DCPD (DCPD-enal) and 36.14 g of isomeric di-formyl derivatives of DCPD (DCPD-dial).

REFERENCE EXAMPLE 5

A catalyst solution was prepared from 150 mL of P-DIPB, 84 mg of $RhAcAc(CO)_2$ (0.3251 mmole), 0.89 g of BISBI (1.618 mmole) and 0.49 g of tribenzylphosphine (TBP) (1.62 mmole) under nitrogen and was charged to the reactor under argon and sealed. The reactor was pressured to 260 psig with hydrogen, carbon monoxide and nitrogen and heated to 95° C. The gas flow rates were 1.20 L/minute hydrogen, 1.58 L/minute carbon monoxide and 2.28 L/minute nitrogen. These flows correspond to the following partial pressures in the feed to the reactor: hydrogen=65 psia and CO=86 psia. 1,7-Octadiene was pumped into the reactor over two hours at 25 mL/hour (18.6 g/hour). The gas flows and the reactor temperature were maintained for an extra two hours. After cooling, the reactor contents were collected under argon and analyzed using GLC techniques. The hydroformylation product solution obtained contained 0.48 grams of C8, 9.03 grams of C9-enal and 39.93 grams of isomeric C10-dial. The C10-dial contained 94.9 percent 1,10-decanedial.

REFERENCE EXAMPLE 6

A catalyst mixture was prepared, as above, using 150 mL of P-DIPB, 84 mg of $RhAcAc(CO)_2$ and 0.60 g of TOP (tri-n-octylphosphine). The reactor was pressured to 260 psig with hydrogen and carbon monoxide and heated to 125° C. The hydrogen and carbon monoxide flows were 1.65 L/minute each, which yields partial pressures of 137 psia each in the feed to the reactor. 1,5-Cyclooctadiene (1,5-COD) (85 percent pure) was pumped into the reactor at 25 mL/hour (22.0 g/hour) over two hours. The gas flows were maintained at the 125° C. temperature an extra two hours. After cooling and draining, the contents of the reactor were analyzed by GLC methods. The hydroformylation product solution contained 0.91 g of isomeric cyclic eight carbon hydrocarbons, 23.89 g of mono-formyl derivatives of which 76 percent was formylcyclooctane and 29.74 g of mixed di-formyl derivatives (COD-dial).

REFERENCE EXAMPLE 7

A catalyst solution was prepared from 84 mg of $RhAcAc(CO)_2$ (0.3251 mmole), 8.52 g of triphenylphosphine (TPP, 32.51 mmole) and 150 mL of P DIPB solvent. The mixture was charged to the reactor under argon, sealed and pressured to 260 psig with hydrogen and carbon monoxide. The reactor was heated to 95° C. and the gas flows were set at 5.00 L/min hydrogen and 1.00 L/minute carbon monoxide which provide hydrogen and carbon monoxide partial pressures in the feed to the reactor of 229 psia and 46 psia, respectively. 1,7-Octadiene was pumped into the reactor at 25 mL/hour (18.6 g/hour) over two hours and kept at the above reactor conditions an extra two hours following the end of the addition. After cooling, the reactor contents were collected and analyzed by GLC techniques. The hydroformylation product solution contained 0.52 g of isomeric C8 compounds, 9.39 g of isomeric C9-enal and 38.36 g of C10-dial. The 1,10 decanedial isomer was 82.2 percent of the total C10-dial fraction.

REFERENCE EXAMPLE 8

Using the procedures described in the preceding examples, 37.3 g of 1,7-octadiene was hydroformylated using the following materials: 84 mg of $RhAcAc(CO)_2$, 0.89 g of BISBI and 150 mL dodecane hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.66 g of isomeric octadiene (C8) compounds, 8.09 g of isomeric noneneal (C9-enal, mono hydroformyled product) and 32.36 g of isomeric decanedialdehyde (C10-dial).

REFERENCE EXAMPLE 9

Using the procedures described in the preceding examples, 37.3 g of 1,7-octadiene was hydroformylated using the following materials: 84 mg of $RhAcAc(CO)_2$, 0.89 g of BISBI and 150 mL p-diisopropylbenzene hydroformylation solvent. The hydroformylation temperature and pressure were 95° C. and 260 psig and the gas flow rates were 1.14 L/minute hydrogen, 1.65 L/minute carbon monoxide and 2.17 L/minute nitrogen. The hydroformylation product solution thus produced contained 0.59 g of isomeric octadiene (C8) compounds, 8.66 g of isomeric noneneal (C9-enal, mono hydroformyled product) and 38.78 g of isomeric decanedialdehyde (C10-dial).

REFERENCE EXAMPLE 10

Using the procedures described in the preceding examples, 74.6 g of 1,7-octadiene, fed at a rate of 50 mL per hour, was hydroformylated using the following materials: 168 mg of $RhAcAc(CO)_2$, 178mg of BISBI and 300 mL p-diisopropylbenzene hydroformylation solvent. The hydroformylation temperature and pressure were 95° C. and 260 psig and the gas flow rates were 1.14 L/minute hydrogen, 1.65 L/minute carbon monoxide and 2.17 L/minute nitrogen. The hydroformylation product solution thus produced contained 1.05 g of isomeric octadiene (C8) compounds, 19.44 g of isomeric noneneal (C9-enal, mono-hydroformyled product) and 82.17 g of isomeric decanedialdehyde (C10-dial).

REFERENCE EXAMPLE 11

Using the procedures described in the preceding examples, 37.3 g of 1,7-octadiene was hydroformylated using the following materials: 84 mg of $RhAcAc(CO)_2$, 0.29 g of tricyclohexylphosphine and 150 mL p-diisopropylbenzene hydroformylation solvent. The hydroformylation temperature and pressure were 115° C. and 260 psig and the gas flow rates were 1.65 L/minute of both hydrogen and carbon monoxide. The hydroformylation product solution thus produced contained 0.14 g of isomeric octadiene (C8) compounds, 0.64 g of isomeric noneneal (C9-enal, mono-hydroformyled product) and 50.20 g of isomeric decanedialdehyde (C10-dial).

REFERENCE EXAMPLE 12

Using the procedures described in the preceding examples, 37.3 g of 1,7-octadiene was hydroformylated using the following materials: 84 mg of $RhAcAc(CO)_2$, 0.72 g of tribenzylphosphine and 150 mL p-diisopropylbenzene hydroformylation solvent. The hydroformylation temperature and pressure were 95° C. and 260 psig and the gas flow rates were 1.65 L/minute of both hydrogen and carbon monoxide. The hydroformylation product solution thus produced contained 0.37 g of isomeric octadiene (C8) compounds, 0.82 g of isomeric noneneal (C9-enal, mono-hydroformyled product) and 49.12 g of isomeric decanedialdehyde (C10-dial).

REFERENCE EXAMPLE 13

Using the procedures described in the preceding examples, 37.3 g of 1,7-octadiene was hydroformylated using the following materials: 84 mg of RhAcAc(CO)$_2$, 0.36 g of trioctylphosphine and 150 mL p-diisopropylbenzene hydroformylation solvent. The hydroformylation temperature and pressure were 125° C. and 260 psig and the gas flow rates were 1.65 L/minute of both hydrogen and carbon monoxide. The hydroformylation product solution thus produced contained 0.26 g of isomeric octadiene (C8) compounds, 1.74 g of isomeric noneneal (C9-enal, mono-hydroformyled product) and 48.82 g of isomeric decanedialdehyde (C10-dial).

REFERENCE EXAMPLE 14

Using the procedures described in the preceding examples, 41.6 g of 4-vinylcyclohexene (VCH) was hydroformylated using the following materials: 84 mg of RhAcAc(CO)$_2$, 1.10 g of tribenzylphosphine and 150 mL p-diisopropylbenzene hydroformylation solvent. The hydroformylation temperature and pressure were 115° C. and 260 psig and the gas flow rates Were 1.65 L/minute of both hydrogen and carbon monoxide. The hydroformylation product solution thus produced contained 0.50 g of isomeric cyclic eight carbon dienes (CC8), 15.38 g of mono-formyl derivatives of VCH (VCH-enal) and 41.18 g of isomeric di-formyl derivatives of VCH (VCH-dial).

REFERENCE EXAMPLE 15

Using the procedures described in the preceding examples, 44.5 g of trans,trans,cis-1,5,9-cyclododecatriene was hydroformylated using the following materials: 84 mg of RhAcAc(CO)$_2$, 1.10 g of tribenzylphosphine and 150 mL p-diisopropylbenzene hydroformylation solvent. The hydroformylation temperature and pressure were 125° C. and 260 psig and the gas flow rates were 1.65 L/minute of both hydrogen and carbon monoxide. The hydroformylation product solution thus produced contained 2.47 g of recovered isomeric cyclic dodecatriene compounds (C12), 13.05 g of isomeric mono-formylcyclododecadiene compounds (C13), 29.86 g of isomeric di-formyl cyclododecene compounds (C14) and 9.17 g of isomeric tri-formyl cyclododecane compounds (C15).

REFERENCE EXAMPLE 16

Using the procedures described in the preceding examples, 37.3 g of 1,7-octadiene was hydroformylated using the following materials: 84 mg of RhAcAc(CO)$_2$, 0.89 g of BISBI and 150 mL tertiary-butylbenzene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.37 g of isomeric octadiene (C8) compounds, 3.48 g of isomeric noneneal (C9-enal, mono hydroformyled product) and 39.41 g of isomeric decanedialdehyde (C10-dial).

REFERENCE EXAMPLE 17

Using the procedures described in the preceding examples, 37.3 g of 1,7-octadiene was hydroformylated using the following materials: 84 mg of RhAcAc(CO)$_2$, 0.89 g of BISBI and 150 mL decahydronaphthalene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.44 g of isomeric octadiene (C8) compounds, 4.56 g of isomeric noneneal (C9-enal, mono hydroformyled product) and 34.85 g of isomeric decanedialdehyde (C10-dial).

REFERENCE EXAMPLE 18

Using the procedures described in the preceding examples, 37.3 g of 1,7-octadiene was hydroformylated using the following materials: 84 mg of RhAcAc(CO)$_2$, 0.89 g of BISBI and 150 mL tetrahydronaphthalene hydroformylation solvent. The hydroformylation temperature and pressure were 95° C. and 260 psig and the gas flow rates were 1.00 L/minute hydrogen and 1.89 L/minute carbon monoxide. The hydroformylation product solution thus produced contained 0.62 g of isomeric octadiene (C8) compounds, 8.82 g of isomeric noneneal (C9-enal, mono-hydroformyled product) and 32.77 g of isomeric decanedialdehyde (C10-dial).

REFERENCE EXAMPLE 19

Using the procedures described in the preceding examples, 37.3 g of 1,7-octadiene was hydroformylated using the following materials: 84 mg of RhAcAc(CO)$_2$, 0.89 g of BISBI and 150 mL p-diisopropylbenzene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.33 g of isomeric octadiene (C8) compounds, 8.79 g of isomeric noneneal (C9-enal, mono hydroformyled product) and 37.91 g of isomeric decanedialdehyde (C10-dial).

REFERENCE EXAMPLE 20

Using the procedures described in the preceding examples, 37.3 g of 1,7-octadiene was hydroformylated using the following materials: 84 mg of RhAcAc(CO)$_2$, 0.89 g of BISBI and 150 mL of mixed triisopropylbenzene isomers as the hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.38 g of isomeric octadiene (C8) compounds, 7.42 g of isomeric noneneal (C9-enal, monohydroformyled product) and 34.62 g of isomeric decanedialdehyde (C10-dial).

REFERENCE EXAMPLE 21

Using the procedures described in the preceding examples, 37.3 g of 1,7-octadiene was hydroformylated using the following materials: 84 mg of RhAcAc(CO)$_2$, 0.89 g of BISBI and 150 mL m isopropylbenzene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.22 g of isomeric octadiene (C8) compounds, 8.74 g of isomeric noneneal (C9-enal, mono hydroformyled product) and 35.86 g of isomeric decanedialdehyde (C10-dial).

REFERENCE EXAMPLE 22

Using the procedures described in the preceding examples, 37.3 g of 1,7-octadiene was hydroformylated using the following materials: 84 mg of RhAcAc(CO)$_2$, 0.89 g of BISBI and 150 mL tetrahydronaphthalene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.60 g of isomeric octadiene (C8) compounds, 9.63 g of isomeric noneneal (C9-enal, mono hydroformyled product) and 28.01 g of isomeric decanedialdehyde (C10-dial).

REFERENCE EXAMPLE 23

Using the procedures described in the preceding examples, 37.3 g of 1,7-octadiene was hydroformylated using the following materials: 84 mg of RhAcAc(CO)$_2$, 0.89 g of BISBI and 150 mL di-(2-ethylhexyl) phthalate hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.20 g of isomeric octadiene (C8) compounds, 7.52 g of isomeric noneneal (C9-enal, mono hydroformyled product) and 35.68 g of isomeric decanedialdehyde (C10-dial).

REFERENCE EXAMPLE 24

Using the procedures described in the preceding examples, 37.3 g of 1,7-octadiene was hydroformylated using the following materials: 84 mg of RhAcAc(CO)$_2$, 0.89 g of BISBI and 150 mL p diisopropylbenzene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.53 g of isomeric octadiene (C8) compounds, 7.73 g of isomeric noneneal (C9-enal, mono hydroformyled product) and 29.77 g of isomeric decanedialdehyde (C10-dial).

REFERENCE EXAMPLE 25

Using the procedures described in the preceding examples, 37.3 g of 1,7 octadiene was hydroformylated using the following materials: 84 mg of RhAcAc(CO)$_2$, 0.89 g of BISBI and 150 mL dodecane hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.40 g of isomeric octadiene (C8) compounds, 9.18 g of isomeric noneneal (C9-enal, mono hydroformyled product) and 28.87 g of isomeric decanedialdehyde (C10-dial).

REFERENCE EXAMPLE 26

Using the procedures described in the preceding examples, 37.3 g of 1,7-octadiene was hydroformylated using the following materials: 84 mg of RhAcAc(CO)$_2$, 0.89 g of BISBI, 0.43 g of triphenylphosphine and 150 mL p-diisopropylbenzene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.80 g of isomeric octadiene (C8) compounds, 10.51 g of isomeric noneneal (C9-enal, mono hydroformyled product) and 33.65 g of isomeric decanedialdehyde (C10-dial).

REFERENCE EXAMPLE 27

Using the procedures described in the preceding examples, 37.3 g of 1,7-octadiene was hydroformylated using the following materials: 84 mg of RhAcAc(CO)$_2$, 0.89 g of BISBI, 0.46 g of tricyclohexylphosphine and 150 mL p-diisopropylbenzene hydroformylation solvent. The hydroformylation temperature and pressure were 95° C. and 260 psig and the gas flow rates were 1.52 L/minute hydrogen, 2.02 L/minute carbon monoxide and 2.90 L/minute nitrogen. The hydroformylation product solution thus produced contained 0.14 g of isomeric octadiene (C8) compounds, 7.86 g of isomeric noneneal (C9-enal, mono hydroformyled product) and 35.96 g of isomeric decanedialdehyde (C10-dial).

The separation process of my invention is further illustrated by the following examples.

EXAMPLE 1

The extraction examples were carried out in a 300 mL, 3-neck, glass flask equipped with a Teflon magnetic stir bar, a thermometer to measure the temperature of the liquid, a septum for the use of a syringe, a heating mantle and a nitrogen bubbler blanket for the system. The flask was charged with 68 mL (51 g) of hydroformylation product solution prepared in Reference Example 8. The aliquot of the product solution contained 197 mg/L (ppm) rhodium [Rh], 2.43 g of C9-enal and 9.81 g of C10-dial hydroformylation products. An extraction solution consisting of 50 mL of a mixture of methanol and water in a volume ratio of 1:1 and prepared from nitrogen purged methanol and water was added to the flask. The mixture was stirred at 25° C. for 30 minutes to reach equilibrium, stirring was stopped, and the mixture was allowed to separate into 2 layers (phases) over a 30 minute period of time. Both the upper phase comprising hydroformylation solvent and the bottom, extraction solution phase were turbid. Samples of each phase were taken with a syringe and chromatographed on a Hewlett Packard Model 5730 capillary FID gas chromatograph. The instrument used a 30 meter DB-1 column (Supelco.) with a programming rate of a 4 minute hold at 70° C. with a programming rate of 8° C./minute to 250° C. The calculations for the weights of hydroformylation products in each phase were carried out using standard procedures using the dodecane as an internal standard for the catalyst layer and methanol as the internal standard for the aqueous layer. The initial volumes of the two phases were used for estimation of the volumes of the two phases at equilibrium to obtain the concentrations of the products in each phase.

The partition coefficients (Kp) were calculated for the C9-enal and C10-dial products for equilibrium between the dodecane hydroformylation solvent and the extraction solution phases at 25° C. The Kp for the C9-enal and the C10-dial were 1.168 and 66.0, respectively.

The two phases in the flask were heated to and maintained at 53° C. with stirring for 30 minutes to reach equilibrium. The mixture was allowed to separate into 2 layers at 53° C. and each layer was sampled and analyzed as described above. The partition coefficients determined for the C9-enal and C10-dial were 0.565 and 8.12, respectively. The partitioning procedure was repeated at 70° C. The partition coefficients determined were 0.327 for the C9-enal 2.89 for the C10-dial.

The fact that the Kp coefficients for the C10-dial products are greater than the corresponding Kp coefficients of the C9-enal products at any given extraction temperature is advantageous since it permits the selective separation of the dialdehyde products from the intermediate mono formyl-mono-olefin intermediate hydroformylation products. The intermediates may be returned to the reactor along with the hydroformylation solution containing the catalyst components. Conventional distillation and gas stripping techniques would remove the lower boiling mono-formyl intermediates prior to removing the higher boiling di-aldehyde target product. The Kp values determined in this example show that raising the extraction temperature results in a decrease in the efficiency of extracting the aldehyde products from the hydroformylation solvent into the extraction solution.

EXAMPLE 2

Example 1 was repeated except that 68 mL of hydroformylation product solution was extracted with 81 mL of a mixture of methanol and water in a methanol:water volume ratio of 1:1.5 and the extractions were performed at 30° C. and at 60° C. The partition coefficients, calculated as described in Example 1, were:

| Extraction Temperature | Partition Coefficient | |
|---|---|---|
| | C9-enal | C10-dial |
| 30° C. | 0.859 | 44.3 |
| 60° C. | 0.453 | 5.11 |

These Kp values show that the use of higher extraction temperatures lowers partition coefficients when the extraction solvent consists of methanol and water in a methanol:water ratio of 1:1.5.

EXAMPLES 3-19 AND COMPARATIVE EXAMPLES 1-11

It is desirable for the hydroformylation solvent to have a low solubility in the extraction solution to minimize the amount of that solvent that must be recovered from the extraction solution containing the aldehyde products. The solubility of the hydroformylation solvent is reflected by the Kp value of the hydroformylation solvent as it partitions in an equilibrium manner into the aqueous extraction solvent.

Using the procedures described in Example 1, the hydroformylation product solutions containing 1,10-decanedial and isomeric decanedial products produced according to the Reference Examples 8, 10 and 16-24 were extracted using varying extraction temperatures and extraction solvents consisting of various combinations of alkanols and water. The partition coefficients of the hydroformylation solvent in each example are shown in Table I. Table I also sets forth the reference example from which the hydroformylation product solution was obtained (HPS, Ref. Example), the amount (mL) of hydroformylation solution used in each example, the alkanol used in each extraction solution (MeOH=methanol, EtOH=ethanol, PrOH=2 propanol, DEG=diethylene glycol), the alkanol:water volume ratio (Ratio), the amount (mL) of extraction solution used in each example and the temperature (Temp., ° C.) at which each extraction was performed. Comparative examples, i.e., examples using a hydroxy compound other than a primary alkanol, are identified by a "C" preceding an example number, e.g., C-1 designates Comparative Example 1.

TABLE I

| Example No. | HPS Ref. Example | Amount | Extraction Solvent | | | Temp. | Partition Coefficient |
|---|---|---|---|---|---|---|---|
| | | | Alkanol | Ratio | Amount | | |
| C-1 | 8 | 68 | DEG. | 1:1 | 50 | 23 | 0.0026 |
| C-2 | 8 | 68 | DEG | 1:1 | 50 | 50 | 0.0028 |
| C-3 | 16 | 62 | DEG | 1:1 | 50 | 23 | 0.0032 |
| C-4 | 17 | 62 | DEG | 1:1 | 50 | 25 | 0.0050 |
| C-5 | 17 | 62 | DEG | 1:1 | 50 | 70 | 0.034 |
| C-6 | 18 | 62 | DEG | 3:1 | 50 | 25 | 0.092 |
| C-7 | 19 | 62 | DEG | 3:1 | 50 | 30 | 0.128 |
| C-8 | 19 | 62 | DEG | 1.5:1 | 62 | 25 | 0.030 |
| 3 | 19 | 62 | MeOH | 3:1 | 50 | 29 | 0.075 |
| 4 | 19 | 62 | MeOH | 3:1 | 50 | 58 | 0.118 |
| 5 | 19 | 62 | MeOH | 1.5:1 | 62 | 58 | 0.050 |
| 6 | 19 | 62 | MeOH | 1.5:1 | 62 | 31 | 0.018 |
| 7 | 20 | 62 | MeOH | 3:1 | 50 | 31 | 0.053 |
| 8 | 20 | 62 | MeOH | 3:1 | 50 | 54 | 0.061 |
| 9 | 20 | 62 | MeOH | 1.5:1 | 62 | 55 | 0.023 |
| 10 | 20 | 62 | MeOH | 1.5:1 | 62 | 35 | 0.0065 |
| 11 | 20 | 62 | MeOH | 1:1 | 75 | 52 | 0.036 |
| 12 | 21 | 62 | MeOH | 3:1 | 50 | 39 | 0.112 |
| 13 | 21 | 62 | MeOH | 1.5:1 | 62 | 51 | 0.035 |
| 14 | 21 | 62 | MeOH | 1.5:1 | 62 | 30 | 0.0167 |
| 15 | 22 | 62 | MeOH | 1.5:1 | 62 | 52 | 0.079 |
| 16 | 23 | 62 | MeOH | 3:1 | 50 | 50 | 0.0448 |
| 17 | 23 | 62 | MeOH | 1:1 | 75 | 50 | 0.0037 |

TABLE I-continued

| Example No. | HPS Ref. Example | Amount | Extraction Solvent | | | Temp. | Partition Coefficient |
|---|---|---|---|---|---|---|---|
| | | | Alkanol | Ratio | Amount | | |
| 18 | 24 | 32 | EtOH | 7:4 | 32 | 52 | 0.033 |
| 19 | 24 | 32 | EtOH | 7:4 | 32 | 32 | 0.009 |
| C-9 | 10 | 62 | PrOH | 3:1 | 50 | 50 | 0.055 |
| C-10 | 10 | 62 | PrOH | 1.5:1 | 62 | 50 | 0.018 |
| C-11 | 10 | 62 | PrOH | 1:1 | 75 | 50 | 0.013 |

Although the data reported in Table I shows that the hydroformylation solvents exhibit desirable partition coefficient values in extraction solutions containing diethylene glycol and 2 propanol, the aldehyde products exhibit poor partition coefficients with respect to such extraction solutions as is shown by the examples below.

EXAMPLES 20-30 AND COMPARATIVE EXAMPLES 12-24

Using the procedures described in Example 1, the hydroformylation product solutions containing C10-dial hydroformylation product and intermediate C9-enal produced according to the Reference Examples 8, 10, 19, 24 and 25 were extracted using varying extraction temperatures and extraction solvents consisting of various combinations of alkanols and water. The partition coefficients of the C9-enal, the C10-dial and, for Examples 34-53, the hydroformylation solvent (H.F.) in each example are shown in Table II. Table II also sets forth the reference example from which the hydroformylation product solution (HPS, Ref. Example) was obtained, the amount (mL) of hydroformylation product solution used in each example, the alkanol used in each extraction solution (MeOH=methanol, EtOH=ethanol, PrOH=2-propanol, DEG=diethylene glycol), the alkanol:water volume ratio (Ratio), the amount (mL) of extraction solution used in each example and the temperature (Temp., °C.) at which each extraction was performed. In Example 42 and 43, the extraction solvent consisted of only diethylene glycol, i.e., no water was present.

For the purpose of comparing extraction efficiencies, the partition coefficients obtained in certain of the above described examples for C9-enal, C10-dial and the hydroformylation solvent by the use of extraction solutions consisting of methanol and water are set forth in Table III. The methanol:water volume ratios and extraction temperatures are repeated in Table III.

TABLE III

| Example No. | Extraction Solution Ratio | Temp. | Partition Coefficient | | |
|---|---|---|---|---|---|
| | | | C9-enal | C10-dial | H.S. |
| 7 | 3:1 | 31 | 2.624 | 32.87 | 0.053 |
| 10 | 1.5:1 | 35 | 0.875 | 16.73 | 0.0065 |
| 12 | 3:1 | 39 | 1.497 | 29.62 | 0.112 |
| 14 | 1.5:1 | 30 | 0.611 | 19.56 | 0.0167 |
| 20 | 1:1 | 25 | 1.168 | 66.01 | — |
| 23 | 1.5:1 | 30 | 0.859 | 44.29 | — |
| 24 | 3:1 | 29 | 1.971 | 33.09 | 0.075 |
| 25 | 3:1 | 58 | 1.041 | 5.65 | 0.118 |
| 26 | 1.5:1 | 58 | 0.245 | 1.273 | 0.050 |
| 27 | 1.5:1 | 31 | 0.527 | 9.565 | 0.018 |

In the examples listed in Table III, the hydroformylation solvent component of the hydroformylation product solutions extracted was one of the preferred hydrocarbon compounds: (1) mixed isomers of triisopropylbenzene, (2) meta-diisopropylbenzene, (3) para diisopropylbenzene or (4) dodecane.

EXAMPLES 31-48

These examples illustrate a preferred embodiment of the extraction process provided by the present wherein

TABLE II

| Example No. | HPS Ref. Example | Amount | Extraction Solvent | | | Temp. | Partition Coefficient | | |
|---|---|---|---|---|---|---|---|---|---|
| | | | Alkanol | Ratio | Amount | | C9-enal | C10-dial | H.S. |
| 20 | 8 | 68 | MeOH | 1:1 | 50 | 25 | 1.168 | 66.1 | — |
| 21 | 8 | 68 | MeOH | 1:1 | 50 | 53 | 0.565 | 8.12 | — |
| 22 | 8 | 68 | MeOH | 1:1.5 | 81 | 60 | 0.453 | 5.11 | — |
| 23 | 8 | 68 | MeOH | 1:1.5 | 81 | 30 | 0.859 | 44.29 | — |
| C-12 | 8 | 68 | DEG | 1:1 | 50 | 23 | 0.36 | 3.76 | 0.0026 |
| C-13 | 8 | 68 | DEG | 1:1 | 50 | 50 | 0.27 | 0.90 | 0.0028 |
| C-14 | 25 | 62 | PrOH | 1:1 | 50 | 23 | 0.285 | 2.190 | 0.0116 |
| C-15 | 25 | 62 | PrOH | 1:1 | 50 | 60 | 0.137 | 0.497 | 0.0097 |
| 24 | 19 | 62 | MeOH | 3:1 | 50 | 29 | 1.971 | 33.09 | 0.075 |
| 25 | 19 | 62 | MeOH | 3:1 | 50 | 58 | 1.041 | 5.65 | 0.118 |
| 26 | 19 | 62 | MeOH | 1.5:1 | 62 | 58 | 0.245 | 1.273 | 0.050 |
| 27 | 19 | 62 | MeOH | 1.5:1 | 62 | 31 | 0.527 | 9.565 | 0.018 |
| C-16 | 19 | 62 | DEG | — | 38 | 58 | 0.595 | 2.354 | 0.128 |
| C-17 | 19 | 62 | DEG | — | 38 | 33 | 0.747 | 3.986 | 0.128 |
| C-18 | 19 | 62 | DEG | 3:1 | 50 | 30 | 0.216 | 1.896 | 0.030 |
| C-19 | 19 | 62 | DEG | 3:1 | 50 | 60 | 0.065 | 0.432 | 0.014 |
| C-20 | 19 | 62 | DEG | 1.5:1 | 62 | 60 | 0.0097 | 0.102 | 0.0061 |
| C-21 | 19 | 62 | DEG | 1.5:1 | 62 | 25 | 0.0159 | 0.381 | 0.0030 |
| 28 | 24 | 32 | EtOH | 3:1 | 25 | 48 | 0.922 | 2.541 | 0.298 |
| 29 | 24 | 32 | EtOH | 3:1 | 25 | 33 | 1.239 | 5.34 | 0.229 |
| 30 | 24 | 32 | EtOH | 7:4 | 32 | 52 | 0.128 | 0.442 | 0.033 |
| C-22 | 10 | 62 | PrOH | 3:1 | 50 | 50 | 0.109 | 0.148 | 0.055 |
| C-23 | 10 | 62 | PrOH | 1.5:1 | 62 | 50 | 0.016 | 0.064 | 0.0182 |
| C-24 | 10 | 62 | PrOH | 1:1 | 75 | 50 | 0.019 | 0.044 | 0.0132 | an alkali metal carboxylate salt is included in the extraction solution. These examples were carried out using the general procedure of Example 1 and the hydroformylation product solution obtained in Reference Example 1.

In each example, 62 mL aliquots of hydroformylation product solution having a rhodium [Rh] concentration of 173 mg/L and containing 2.65 g of C9-enal isomers, 12.05 g of C10-dial isomers and 38.99 g of p-diisopropylbenzene hydroformylation solvent were added to the 300 mL flask. The flask also was charged with an extraction solution consisting of 37 mL methanol and 12 mL of water. Each experiment employed an extraction temperature of 50° C., an agitation period of 30 minutes and a phase separation period of 5 minutes followed by sampling of the extraction solution phase. One mL aliquots of the lower, extraction solution phase was sampled for Rh analysis.

In examples 31, 37 and 43, no alkali metal carboxylate was added to the extraction mixture. In Examples 32–36, varying amounts of an aqueous solution containing 18,400 mg/L sodium as the 2-ethylhexanoate salt were added to the agitated extraction mixture; in Examples 38–42, varying amounts of an aqueous solution containing 9200 mg/L sodium as the oleate salt were added to the agitated extraction mixture; and in Examples 44–48, varying amounts of an aqueous solution containing 18,400 mg/L sodium as the n butyrate salt were added to the agitated extraction mixture.

The results of these experiments are shown in Table IV wherein Na Conc. and Rh Conc. are the sodium [Na] and rhodium [Rh] concentrations in mg/L in the extraction solution phase. Also set forth in Table IV are the partition coefficients obtained for the C9-enal isomers, C10-dial isomers and the p diisopropylbenzene hydroformylation solvent (H.S.) in each example.

TABLE IV

| Example No. | Na Conc. | Rh Conc. | Partition Coefficient | | |
|---|---|---|---|---|---|
| | | | C9-enal | C10-dial | H.S. |
| 31 | 0 | 120 | 0.859 | 5.842 | 0.096 |
| 32 | 82 | 54 | 0.857 | 4.982 | 0.125 |
| 33 | 164 | 37 | 0.939 | 6.626 | 0.115 |
| 34 | 327 | 28 | 0.908 | 6.822 | 0.131 |
| 35 | 653 | 20 | 0.913 | 7.197 | 0.137 |
| 36 | 1307 | 12 | 0.592 | 5.201 | 0.063 |
| 37 | 0 | 56 | 0.811 | 5.869 | 0.064 |
| 38 | 82 | 6 | 0.894 | 7.326 | 0.083 |
| 39 | 164 | 5 | 0.801 | 7.444 | 0.062 |
| 40 | 327 | 4 | 0.830 | 7.063 | 0.083 |
| 41 | 653 | 4 | 0.747 | 8.568 | 0.052 |
| 42 | 1307 | 3.6 | 0.702 | 6.951 | 0.063 |
| 43 | 0 | 72 | 0.895 | 6.767 | 0.074 |
| 44 | 82 | 39 | 0.848 | 7.016 | 0.063 |
| 45 | 164 | 32 | 0.854 | 6.426 | 0.073 |
| 46 | 327 | 25 | 0.692 | 5.590 | 0.053 |
| 47 | 653 | 22 | 0.708 | 6.679 | 0.051 |
| 48 | 1307 | 15 | 0.554 | 4.869 | 0.038 |

The data presented in Table IV show that increasing the concentration of the sodium carboxylate salt in the extraction solution lowers the amount of rhodium that is extracted from the hydroformylation product solution into the extraction solution. These data also show that the most effective sodium carboxylate salt is sodium oleate. The short, carbon chain n-butyrate sodium salt was the least effective. Thus, the preferred alkali metal carboxylate salts for use in this embodiment of the invention are those having four or more carbon atoms in the carboxylate residue of the salt. The Table IV data further show that the Kp values for the C9-enal, C10-dial and p-diisopropyl hydroformylation solvent do not change significantly with different sodium concentrations indicating that the presence of the salts does not affect detrimentally the extraction of the products into the extraction solution.

EXAMPLE 49-51

These experiments employed the general procedure described above for Examples 31–48 and the hydroformylation product solution produced in Reference Example 9 which had a rhodium concentration of 176 mg/L. The 300 mL extraction flask was charged with (1) 62 mL of the hydroformylation product solution which contained 2.91 g C9-enal isomers, 12.58 g C10-dial isomers and 38.53 g of p diisopropylbenzene hydroformylation solvent and (2) an extraction solution consisting of 37 mL methanol and 27 mL water.

The extractions were performed as described in Example 31–48 with the addition in Examples 50 and 51 of varying amounts of the aqueous sodium oleate solution referred to above. The results obtained are set forth in Table V.

TABLE V

| Example No. | Na Conc. | Rh Conc. | Partition Coefficient | | |
|---|---|---|---|---|---|
| | | | C9-enal | C10-dial | H.S. |
| 49 | 0 | 18.6 | 0.224 | 1.947 | 0.0164 |
| 50 | 100 | 2.6 | 0.224 | 1.886 | 0.0210 |
| 51 | 200 | <1 | 0.191 | 1.372 | 0.0210 |

The data of the Table VI examples show that the higher the concentration of water in the extraction solution in these example versus the Example 31–48 that used a methanol:water volume ratio of 3:1 renders the sodium carboxylate salt more effective in suppressing the extraction of Rh into the extraction solution. The Rh concentration was below the detection limit in Example 51.

EXAMPLES 52–78

These examples show the effect of sodium 2-ethyl hexanoate concentration on the concentration of rhodium in the aqueous extraction phase for different hydroformylation product solutions resulting from the hydroformylation of 1,7-octadiene. The extraction, sampling and analytical procedures used were substantially the same as those described in Examples 31–48. The extractions were carried out at 50° C. using 62 mL of each hydroformylation product solution and 50 mL of an extraction mixture consisting of a 3:1 volume ratio of methanol and water. Varying amounts of an aqueous solution containing 18,400 mg/L sodium as the 2-ethylhexanoate salt were added to each agitated extraction mixture except in Examples 52, 56, 60, 64, 68, 72 and 76 in which no sodium 2-ethylhexanoate was added.

The results of these experiments are shown in Table VI wherein Na Conc. and Rh Conc. are the sodium [Na] and rhodium [Rh] concentrations in mg/L in the extraction solution phase and HPS, Ref. Example identifies the reference example from which the hydroformylation product solution used in each example was obtained.

TABLE VI

| Example No. | HPS, Ref. Example | Na Conc. | Rh Conc. |
|---|---|---|---|
| 52 | 1 | 0 | 120 |
| 53 | 1 | 82 | 54 |
| 54 | 1 | 164 | 37 |
| 55 | 1 | 327 | 28 |
| 56 | 11 | 0 | 7.6 |

TABLE VI-continued

| Example No. | HPS, Ref. Example | Na Conc. | Rh Conc. |
|---|---|---|---|
| 57 | 11 | 82 | 5.2 |
| 58 | 11 | 164 | 2.6 |
| 59 | 11 | 327 | 1.4 |
| 60 | 12 | 0 | 6.2 |
| 61 | 12 | 82 | 5.4 |
| 62 | 12 | 164 | 5.6 |
| 63 | 12 | 327 | 5.4 |
| 64 | 7 | 0 | 7.6 |
| 65 | 7 | 82 | 2.0 |
| 66 | 7 | 164 | 2.2 |
| 67 | 7 | 327 | 1.8 |
| 68 | 13 | 0 | 1.2 |
| 69 | 13 | 82 | 1.0 |
| 70 | 13 | 164 | <1 |
| 71 | 13 | 327 | <1 |
| 72 | 26 | 0 | 30 |
| 73 | 26 | 82 | 10 |
| 74 | 26 | 164 | 8.2 |
| 75 | 26 | 327 | 6.8 |
| 76 | 27 | 0 | 10 |
| 77 | 27 | 82 | 1.8 |
| 78 | 27 | 164 | 2.8 |

The data presented in Table VI show that the addition of alkali metal carboxylate salts to the aqueous methanol extraction solution generally suppresses rhodium extraction into the extraction solution in various hydroformylation product solutions produced by different low pressure, hydroformylation production systems. Such systems utilize a catalyst system comprising rhodium and bidentate phosphines such as BISBI, monobasic triorganophosphines such as TCHP, TBP, TPP and TOP and mixtures of bidentate and mono basic organophosphine compounds. The partition coefficients obtained for the C9-enal C10-dial isomers and the p-diisopropylbenzene hydroformylation solvent (H.S.) in preceding Examples 52, 54, 56, 58, 60, 62, 64, 66, 68 and 70 are set forth in Table VII.

TABLE VII

| Example No. | Partition Coefficients | | |
|---|---|---|---|
| | C9-enal | C10-dial | H.S. |
| 52 | 0.859 | 5.842 | 0.115 |
| 54 | 0.939 | 6.626 | 0.073 |
| 56 | 0.663 | 3.534 | 0.081 |
| 58 | 0.620 | 4.045 | 0.073 |
| 60 | 0.533 | 3.900 | 0.071 |
| 62 | 0.894 | 3.805 | 0.067 |
| 64 | 0.538 | 4.450 | 0.056 |
| 66 | 0.595 | 4.342 | 0.072 |
| 68 | 0.699 | 4.195 | 0.076 |
| 70 | 0.813 | 4.862 | 0.060 |

The data of Table VII show that the presence of sodium is not detrimental to efficiency of the extraction of the aldehyde.

EXAMPLES 79-82

These examples illustrate the separation of a mixture of mono- and di-aldehydes obtained by the hydroformylation of 4-vinylcyclohexene (VCH) in the presence of a catalyst system comprising rhodium and trioctylphosphine and p-diisopropylbenzene hydroformylation solvent. These examples were carried out at 50° C. using the general procedure of Examples 31-48 and the hydroformylation product solution obtained in Reference Example 3.

A 60 mL aliquot of hydroformylation product solution having a rhodium [Rh] concentration of 181 mg/L and containing 11.81 g of VCH mono aldehyde products, 4.65 g of VCH di-aldehyde products and 36.45 g of p-diisopropylbenzene hydroformylation solvent was extracted initially (Example 79) with an extraction solution consisting of 40 mL methanol and 10 mL water containing 5.0 mg [Na] in the form of sodium 2-ethylhexanoate. The extraction of the aliquot of hydroformylation solution was repeated three times (Examples 80, 81 and 82) with the addition of 10 mL of water prior to each extraction. Each extraction employed an agitation period of 30 minutes and a phase separation period of 5 minutes followed by sampling of the extraction solution phase. One mL aliquots of the lower, extraction solution phase was sampled for Rh analysis.

The results obtained are shown in Table VIII wherein the rhodium concentration in mg [Rh] per liter (Rh Conc.) and the partition coefficients for the VCH mono-aldehyde products (VCH monoal), the VCH di-aldehyde products (VCH dial) and the p-diisopropylbenzene hydroformylation solvent (H.S.) are reported.

TABLE VIII

| Example No. | Rh Conc. | Partition Coefficient | | |
|---|---|---|---|---|
| | | C9-enal | C10-dial | H.S. |
| 79 | <1 | 0.779 | 2.485 | 0.0859 |
| 80 | <1 | 0.230 | 0.858 | 0.0233 |
| 81 | 3.0 | 0.0922 | 0.377 | 0.0050 |
| 82 | <1 | 0.0656 | 0.285 | 0.0017 |

EXAMPLES 83-85

The procedure described in Examples 79-82 was repeated using the hydroformylation product solution obtained by hydroformylating dicyclopentadiene (DCPD) in the presence of a catalyst system comprising rhodium and tricyclohexylphosphine and p-diisopropylbenzene hydroformylation solvent (Reference Example 4). The 60 mL of hydroformylation product solution used had a rhodium concentration of 182 mg/L and contained 9.15 g mono-formyl-DCPD products (DCPD-mono-al), 11.16 g di-formyl-DCPD products (DCPD-dial) and 35.20 g p-diisopropylbenzene. The results obtained are shown in Table IX.

TABLE IX

| Example No. | Rh Conc. | Partition Coefficient | | |
|---|---|---|---|---|
| | | DCPD mono-al | DCPD dial | H.S. |
| 83 | 2.0 | 0.409 | 2.284 | 0.0724 |
| 84 | <1 | 0.148 | 0.846 | 0.0469 |
| 85 | <1 | 0.0603 | 0.44 | 0.0269 |

EXAMPLES 86 AND 87

The procedure described in Examples 79-82 was repeated using 62 mL of the hydroformylation product solution obtained by hydroformylating 1,5,9-cyclododecatriene (CDDT) in the presence of a catalyst system comprising rhodium and tricyclohexylphosphine and p-diisopropylbenzene hydroformylation solvent (Reference Example 2). The 62 mL of hydroformylation product solution had a rhodium [Rh] concentration of 171 mg/L and contained 3.11 g of CDDT mono-aldehyde products CDDT-mono-al), 10.33 g of CDDT di-aldehyde products (CDDT-dial), 2.74 g of CDDT tri-aldehyde products (CDDT-trial) and 39.71 g of p-diisopropylbenzene hydroformylation solvent. In Example 86, 37 mL methanol, 12 mL water and 5.0 mg [Na] in the form of sodium 2-ethylhexanoate were added to the flask. The extraction employed a temperature of 25° C., an agitation period of 30 minutes and a phase separation period of 5 minutes followed by sampling of the extraction solution phase. One mL aliquots of the lower, extraction solution phase was sampled for Rh analysis. Example 87 was carried out by adding 10 mL methanol to the extraction mixture resulting from Example 86 and then repeating the extraction, sampling and analytical procedures. The results obtained are shown in Table X.

TABLE X

| Example No. | Rh Conc. | Partition Coefficient | | | |
|---|---|---|---|---|---|
| | | CDDT mono-al | CDDT dial | CDDT trial | H.S. |
| 86 | <1 | 0.0861 | 0.827 | 13.35 | 0.0297 |
| 87 | 1.2 | 0.293 | 2.082 | 22.05 | 0.077 |

Examples 86 and 87 show that the high boiling, triformyl derivatives of 1,5,9-cyclododecatriene are selectively extracted relative to the mono and diformyl derivatives. This selective extraction permits recycling of the mono and di formyl precursors to the hydroformylation reactor along with the rhodium/phosphine catalyst system.

Examples 88614 95 illustrate yet another embodiment of the process of the present invention wherein extraction solution containing dissolved rhodium is back-extracted with either hydroformylation solvent or olefinic feedstock to reduce the concentration of rhodium in the extraction solution. These examples also show that the counter current back extraction can raise the ratio of the desired di-aldehyde product to mono aldehyde product in the extraction solution.

EXAMPLES 88-90

The general procedure described in Examples 31-48 was used to extract 60.5 mL of hydroformylation product solution obtained by the hydroformylation of 1,7 octadiene in the presence of a catalyst system comprising rhodium and BISBI phosphine (Reference Example 9). The 60.5 mL of hydroformylation product solution had a rhodium concentration of 176 mg/L and contained 2.91 g of C9-enal, 12.58 g of C10-dial and 38.53 g of p-diisoropylbenzene hydroformylation solvent. The extraction flask was charged with the hydroformylation product solution, 37 mL methanol, 12 mL water and 19.5 g [Na] provided as sodium oleate.

For Example 88, the extraction mixture was stirred at room temperature for 30 minutes and then drained into a calibrated, addition funnel and allowed to stand for about five minutes to permit phase separation. The volume of the hydroformylation product solution (organic) phase was 45 mL and the volume of the extraction solution phase was 65 ml. Samples of each phase were taken for rhodium and product composition analyses.

For Example 89, the extraction solution phase separated in Example 88 was added to a clean 250 mL flask along with 30 mL of p-diisopropylbenzene and the mixture was stirred at 50° C. for 30 minutes, was allowed to stand at 50° C. for about 5 minutes to permit phase separation and then each phase was separated and analyzed for composition and rhodium concentration.

For Example 90, the extraction solution separated in Example 89 was added to a clean 250 mL flask along with another 30 mL of p-diisopropylbenzene hydroformylation solvent. The mixture was agitated at 50° C. for thirty minutes, allowed to stand at 50° C. for 5 minutes to permit phase separation and each phase was analyzed for composition and rhodium concentration. The results of the analyses for rhodium (mg Rh per liter) are presented in Table XI.

TABLE XI

| Example No. | Rhodium Concentration | |
|---|---|---|
| | Organic Phase | Extraction Solution Phase |
| 88 | 235 | 5.2 |
| 89 | 7.2 | 1.6 |
| 90 | 1.2 | 1.0 |

The data reported in Table XI show that the back-extraction with p-diisopropylbenzene reduces the concentration of rhodium in the extraction solution phase.

EXAMPLES 91-93

These examples demonstrate the use of the hydroformylation solvent p-diisopropylbenzene as a primary back extraction solvent and the di-olefin 1,7-octadiene as a secondary back extraction solvent. This scheme would be useful in a counter-current extraction method for recycling recovered hydroformylation product solution as well as in using the olefinic feed to the reactor as a back extraction solvent for recovering soluble rhodium from the methanol/water extract.

Example 91 was carried out using the procedure described in Examples 88. The flask was charged with 62 mL of a hydroformylation product solution (Reference Example 10) having a rhodium concentration 166 mg/L and containing 3.01 g of C9-enal, 12.69 g of C10-dial and 37.84 grams of p-diisopropylbenzene. Methanol (37 ml), water (16 ml) and 78 mg Na (as sodium 2-ethylhexanoate) were added to the flask. This mixture was stirred at 50° C. for 30 minutes and then allowed to stand for 5 minutes at 50° C. to permit phase separation. The hydroformylation product solution (organic) phase and the extraction solution phase were both sampled and analyzed for rhodium concentration. The 2 phases were drained into a clean, graduated addition funnel and the volumes of the two phases were measured. The volume of the organic layer was 43 mL and the extraction solution layer was 62 mL.

For Example 92, the extraction solution phase produced in Example 91 was added to a clean, 250 mL flask along with 30 mL of p-diisopropylbenzene and the mixture was stirred at 50° C. for 30 minutes and then allowed to separate into two phases. The two phases were analyzed for rhodium concentration and composition. The mixture was drained into a clean addition funnel to separate the two phases. For Example 93, the extraction solution phase of Example 92 and 30 mL of 1,7-octadiene were added to a clean, 250 mL flask. This mixture was stirred at 50° C. for 30 minutes and then allowed to separate into two phases which were analyzed for rhodium concentration. The results of the analyses for rhodium (mg Rh per liter) are presented in Table XII.

TABLE XII

| Example No. | Rhodium Concentration | |
|---|---|---|
| | Organic Phase | Extraction Solution Phase |
| 91 | 216 | 6.2 |
| 92 | 7.0 | 1.0 |
| 93 | <1 | <1 |

The amounts (g) of C9-enal, C10-dial in the sample of hydroformylation product solution initially extracted and in the methanol/water extraction solutions resulting from Examples 91, 92 and 93 are given in Table XIII. The ratio given in Table XIII is the weight ratio of C10-dial:C9-enal.

TABLE XIII

| Example No. | Composition of Extraction Solution | | Ratio |
|---|---|---|---|
| | C9-enal | C10-dial | |
| 91 | 1.39 | 11.67 | 8.40 |
| 92 | 0.51 | 9.21 | 18.06 |
| 93 | 0.18 | 6.11 | 33.94 |

The data reported in Tables XII and XIII show that the concentration of rhodium in the extraction solution was lowered below detection limits and that the decanedial was selectively extracted by the back-extraction procedure described.

EXAMPLES 94 AND 95

The general procedure described in Examples 88-90 was used to extract 62 mL of hydroformylation product solution obtained by the hydroformylation of 1,7-octadiene in the presence of a catalyst system comprising rhodium and BISBI phosphine (Reference Example 24). The 62 mL of hydroformylation product solution had a rhodium concentration of 204 mg/L and contained 3.03 g of C9-enal, 11.29 g of C10-dial and 39.17 g of p-diisopropylbenzene hydroformylation solvent. The extraction flask was charged with the hydroformylation product solution, 37 mL methanol and 12 mL water.

For Example 94, the extraction mixture was stirred at 25° C. for 15 minutes, allowed to separate into 2 phases and the 2 phases were sampled and analyzed for rhodium concentration and composition. The 2 phases were transferred to a calibrated, addition funnel. The volume of the hydroformylation product solution (organic) phase was 45 mL and the volume of the extraction solution phase was 60 ml.

For Example 95, the extraction solution phase produced in Example 94 was added to a clean 250 mL flask along with 30 mL of p-diisopropylbenzene and the mixture was stirred at 50° C. for 30 minutes, was allowed to stand at 50° C. for about 5 minutes to permit phase separation and then each phase was separated and analyzed for composition and rhodium concentration.

The results of the analyses for rhodium (mg Rh per liter) are presented in Table XIV.

TABLE XIV

| Example No. | Rhodium Concentration | |
|---|---|---|
| | Organic Phase | Extraction Solution Phase |
| 94 | 195 | 37 |
| 95 | 24 | 33 |

Example 94 and 95 show that the back extraction with p-diisopropylbenzene is not as efficient for recovering rhodium from the initial extraction solution extract when no sodium carboxylate salt is used.

EXAMPLE 96

This example illustrates the extraction of a high boiling hydroformylation product solution followed by the removal by distillation overhead of the methanol component of the methanol/water extraction solution to obtain a 2-phase mixture in the distillation base of water and high boiling aldehyde product.

The general procedure described in Examples 31-48 was used to extract 62 mL of hydroformylation product solution obtained by the hydroformylation of 1,7-octadiene in the presence of a catalyst system comprising rhodium and BISBI phosphine (Reference Example 10). The 62 mL of hydroformylation product solution had a rhodium concentration of 165 mg/L and contained 2.96 g of C9-enal, 12.63 g of C10-dial and 37.93 g of p-diisopropylbenzene hydroformylation solvent. The extraction flask was charged with the hydroformylation product solution, 37 mL methanol, 16 mL water and 78 mg [Na] provided as sodium 2 ethylhexanoate.

The extraction mixture was stirred at 25° C. for 30 minutes and then allowed to separate into 2 phases. The extraction solvent phase was back extracted twice with 30 mL of p-diisopropylbenzene as described in Examples 88-90. The extraction solvent phase then was transferred to a distillation apparatus and heated at ambient pressure under nitrogen to distill off methanol until the overhead temperature reached 100° C. Heating was discontinued and the residual mixture separated into 2 phases. The upper, organic phase had a net weight of 9.25 g and contained 8.27 grams of predominantly 1,10-decanedial, 0.36 grams of mixed C9-enal, 0.62 grams of p-diisopropylbenzene and a trace of methanol.

The following examples illustrate another embodiment of the present invention which provides a means for the manufacture of alkanols, including diols and triols, comprising the steps of (1) recovering a high boiling aldehyde product in an alkanol/water phase according to the extraction process described and illustrated in detail hereinabove and (2) contacting the alkanol/water phase with hydrogen in the presence of a hydrogenation catalyst under hydrogenation conditions of temperature and pressure.

EXAMPLES 97-102

These examples used the hydroformylation product solutions produced in Reference Examples 110, 5, 7, 13, 12 and 11 wherein 1,7-octadiene was hydroformylated in the presence of a catalyst system comprising rhodium and a phosphine and p-diisopropylbenzene hydroformylation solvent. The extraction apparatus consisted of a 500 mL, three neck flask equipped with a magnetic stirrer, heating mantle, thermometer and nitrogen atmosphere. All manipulations through the completion of the hydrogenation reaction were carried out under nitrogen.

The flask was charged with 120 mL of hydroformylation product solution, 90 mL methanol, 30 mL water and 48 mg of [Na] charged as sodium 2 ethylhexanoate. The mixture was stirred at 50° C. for 30 minutes and then added to a separatory funnel to separate the two layers. The bottom layer consisting of the methanol/water phase containing aldehyde product was transferred to another separatory funnel that contained 30 ml of toluene to back-extract the methanol/water extract. The back-extracted methanol/water extract was separated from the toluene and hydrogenated as described below.

The amounts (g) of the C9-enal and C10-dial products present in each 62 mL aliquot of hydroformylation product solution used and the reference example from which each was obtained are set forth in Table XV. Also listed in Table XV under "% Linear" is the weight percent 1,10-decanedial based on the total weight in grams of the C10-dial compounds which also include 2-methyl-1,9-nonanedial and 2,7-dimethyl-1,8-octanedial.

TABLE XV

| Example No. | Reference Example | C9-enal | C10-dial | % Linear |
|---|---|---|---|---|
| 97 | 10 | 5.76 | 24.36 | 96.6 |
| 98 | 5 | 6.12 | 24.17 | 94.9 |
| 99 | 7 | 6.02 | 22.98 | 82.2 |
| 100 | 13 | 1.42 | 29.39 | 44.8 |
| 101 | 12 | 0.74 | 30.03 | 37.9 |
| 102 | 11 | 0.58 | 29.28 | 30.0 |

The back-extracted methanol/water extract and 2.0 g of neutralized Raney nickel hydrogenation catalyst was charged to a 300 mL, stainless steel, magnetically driven autoclave with a Rushton-type stirrer (Autoclave Engineers Magnedrive Autoclave). The autoclave was pressured to 500 psig with hydrogen and heated at 130° C. for 2 hours. The autoclave was cooled, de-pressurized and the crude hydrogenation product was filtered and the filtrate stripped on a rotary evaporator at 70° C. at 5 torr to remove the water and methanol. The hydrogenation products were analyzed by gas liquid chromatography. The product of Example 97 was a crystalline solid whereas the products of Examples 98-101 were tacky solids and the product of Example 102 was a viscous liquid.

The amounts (g) of nonanol products, 2,7-dimethyl octane-1,8-diol (1,8-Diol), 2-methylnonane 1,9-diol (1,9-Diol) and 1,10 decanediol (1,10-Diol) present in the hydrogenation product obtained in each example are listed in Table XVI. Also listed in Table XVI under "% Linear" is the weight percent 1,10-decanediol based on the total weight of the diols.

TABLE XVI

| Example No. | Nonanol | 1,8-Diol | 1,9-Diol | 1,10-Diol | % Linear |
|---|---|---|---|---|---|
| 97 | 0.66 | 0.00 | 0.53 | 19.93 | 97.4 |
| 98 | 0.78 | 0.00 | 1.15 | 18.92 | 94.3 |
| 99 | 0.78 | 0.15 | 3.83 | 15.75 | 79.7 |
| 100 | 0.00 | 2.76 | 13.10 | 8.06 | 33.7 |
| 101 | 0.00 | 3.68 | 13.99 | 8.24 | 31.8 |
| 102 | 0.00 | 5.74 | 14.85 | 5.21 | 20.2 |

EXAMPLES 103-106

These examples demonstrate the use of the combination extraction/hydrogenation process for the preparation of other diol and triol products from the hydroformylation product solutions produced in Reference Examples 6, 14, 4 and 15. The apparatus used was the same as that described in Examples 97-102.

The flask was charged with 120 mL of hydroformylation product solution, 100 mL methanol, 25 mL water and 12 mg of [Na] charged as sodium 2-ethylhexanoate. In Example 103, 40 mL of hexane also was charged to the flask to modify the density of the organic phase to permit phase separation.

The mixture was stirred at 50° C. for 30 minutes and then added to a separatory funnel to separate the two layers. The bottom layer consisting of the methanol/water phase containing aldehyde product was transferred to another separatory funnel that contained 30 ml of toluene to back extract the methanol/water extract. The back extracted methanol/water extract was separated from the toluene and hydrogenated as described below.

The amounts (g) of aldehydes contained in the 120-mL aliquots of hydroformylation product solutions used in each example were:

Example 103: 16.07 g mono-aldehydes and 20.27 g di-aldehydes derived from 1,5-cyclooctadiene (Reference Example 6)

Example 104 9.51 g mono-aldehydes and 25.46 g di-aldehydes derived from 4-vinylcyclohexene (Reference Example 14)

Example 105 13.19 g mono-aldehydes and 16.69 g di-aldehydes derived from dicyclopentadiene (Reference Example 15)

Example 106 21.91 g mono-aldehydes, 5.54 di-aldehydes and 2.97 tri-aldehydes derived from trans,-trans,cis-1,5,9-cyclododecatriene (Reference Example 4)

The back extracted methanol/water extracts were hydrogenated, stripped of methanol and water and analyzed according to the procedures described in Examples 97-102. The amounts of cyclic methanol products obtained in each example were:

Example 103: 1.58 g cyclooctylmethanol and 10.17 g cyclooctanedimethanol

Example 104: 1.99 g isomeric hydroxypropylcyclohexane compounds and 18.11 g isomeric hydroxymethyl,hydroxypropylcyclohexane compounds Example 105: 2.81 g dicyclopentanemethanol and 12.22 g dicyclopentanedimethanol Example 106 0.40 g cyclododecylmethanol, 12.22 g cyclododecanedimethanol and 2.97 g cyclododecanetrimethanol The invention has been described in detail with particular reference to preferred embodiments thereof, but it will be understood that variations and modifications may be effected within the spirit and scope of the invention.

I claim:

1. Process for the recovery of an aldehyde product from a hydroformylation product solution comprising (i) a high-boiling aldehyde, (ii) hydroformylation catalyst components comprising rhodium and an organophosphine compound, and (iii) a hydroformylation solvent selected from the group consisting of alkanes having about 5 to 20 carbon atoms, benzene, toluene, xylene isomers, tetrahydronaphthalene, decahydronaphthalene and dialkyl benzenedicarboxylate esters, by the steps of:
   (1) intimately contacting the hydroformylation product solution with an extraction solution comprising a primary alkanol and water to form a 2-phase mixture; and
   (2) separating the mixture of step (1) to obtain: (a) a hydroformylation solvent phase containing catalyst components; and (b) an alkanol/water phase containing the high-boiling aldehyde.

2. Process according to claim 1 for the recovery of an aldehyde product from a hydroformylation product solution comprising (i) an aldehyde having a boiling point of at least 125° C. at atmospheric pressure, (ii) hydroformylation catalyst components comprising rhodium and an organophosphine compound, and (iii) a hydroformylation solvent by the steps of:
   (1) intimately contacting the hydroformylation product solution with an extraction solution comprising a primary alkanol having 1 to 3 carbon atoms and water to form a 2 phase mixture; and
   (2) separating the mixture of step (1) to obtain:
      (a) a hydroformylation solvent phase containing catalyst components; and
      (b) an alkanol/water phase containing the aldehyde;

wherein the volume ratio of primary alkanol to water of the extraction solution is about 20:1 to 1:20 and the difference between the densities of the hydroformylation product solution and the extraction solution is at least 0.02 g/mL.

3. Process for the recovery of an aldehyde product from a hydroformylation product solution comprising (i) an aldehyde having a boiling point of at least 125° C., (ii) hydroformylation catalyst components comprising rhodium and an organophosphine compound, and (iii) a hydroformylation solvent selected from alkanes having about 5 to 20 carbon atoms, alkyl-substituted benzenes having about 9 to 15 carbon atoms, tetrahydronaphthalene, and decahydronaphthalene comprising the steps of:
   (1) intimately contacting the hydroformylation product solution with an extraction solution comprising methanol and water at a temperature of about 20 to 60° C. to form a 2 phase mixture; and
   (2) separating the mixture of step (1) to obtain:
      (a) a hydroformylation solvent phase containing catalyst components; and
      (b) a methanol/water phase containing the aldehyde;
wherein the volume ratio of methanol to water of the extraction solution is about 5:1 to 1:1 and the difference between the densities of the hydroformylation product solution and the extraction solution is at least 0.05 g/mL.

4. Process according to claim 3 wherein the process includes (i) heating the methanol/water of step (2)(b) to vaporize at least 50 weight percent of the methanol and form a liquid phase of the aldehyde and (ii) separating the aldehyde from the liquid phase.

5. Process according to claim 3 wherein the aldehyde has the general formula:

wherein
   $R^1$ is straight or branched chain alkyl of about 5 to 8 carbon atoms;
   $R^2$ is straight or branched chain alkylene having about 2 to 18 carbon atoms; and
   $R^3$ is hydroxy, alkoxy of up to about 4 carbon atoms, alkanoyloxy of up to about 4 carbon atoms, carboxyl or alkoxycarbonyl of 2 to about 10 carbon atoms.

6. Process according to claim 3 wherein the aldehyde has the general formula

wherein $R^4$ is straight or branched chain alkylene having about 5 to 20 carbon atoms.

7. Process according to claim 3 wherein the aldehyde has the general formula

wherein
   $R^5$ is cycloalkylene having about 5 to 12 carbon atoms; and $R^6$ is formyl, formylethyl, carboxyl or alkoxy carbonyl of 2 to about 10 carbon atoms.

8. Process according to claim 3 wherein the aldehyde is selected from decanedials, 4-(2-formylethyl)cyclohexanecarboxaldehyde, 1,4-cyclohexanedicarboxaldehyde, 4-formylcyclohexanecarboxylic acid, dimethyl 4-formylcyclohexanedicarboxylate, 1,4-cyclooctanedicarboxaldehyde, 1,5,9-cyclododecanetricarboxaldehyde, 3-(5,5-dimethyl-1,3-dioxanyl) propionaldehyde, 2-(formylnorbornanyl)acetaldehyde.

9. Process for the recovery of an aldehyde product from a hydroformylation product solution comprising (i) a high-boiling aldehyde, (ii) hydroformylation catalyst components comprising rhodium and an organophosphine compound, and (iii) a hydroformylation solvent selected form the group consisting of alkanes having about 5 to 20 carbon atoms, benzene, toluene, xylene isomers, alkyl-substituted benzenes having about 9 to 15 carbon atoms, tetrahydronaphthalene, decahydronaphthalene and dialkyl benzenedicarboxylate esters, by the steps of:
   (1) intimately contacting the hydroformylation product solution with an extraction solution comprising a primary alkanol, water and a salt of a carboxylic acid to form a 2-phase mixture; and
   (2) separating the mixture of step (1) to obtain:
      (a) a hydroformylation solvent phase containing catalyst components; and
      (b) an alkanol/water phase containing the high-boiling aldehyde.

10. Process according to claim 9 for the recovery of an aldehyde product from a hydroformylation product solution comprising (i) an aldehyde having a boiling point of at least 125° C., (ii) hydroformylation catalyst components comprising rhodium and an organophosphine compound, and (iii) a hydroformylation solvent by the steps of:
   (1) intimately contacting the hydroformylation product solution with an extraction solution comprising a primary alkanol having 1 to 3 carbon atoms, water and an alkali metal salt of a carboxylic acid to form a 2-phase mixture; and
   (2) separating the mixture of step (1) to obtain:
      (a) a hydroformylation solvent phase containing catalyst components; and
      (b) an alkanol/water phase containing the aldehyde;
wherein the volume ratio of primary alkanol to water of the extraction solution is about 20:1 to 1:20 and the difference between the densities of the hydroformylation product solution and the extraction solution is at least 0.05 g/mL.

11. Process for the recovery of an aldehyde product from a hydroformylation product solution comprising (i) an aldehyde having a boiling point of at least 125° C., (ii) hydroformylation catalyst components comprising rhodium and an organophosphine compound, and (iii) a hydroformylation solvent selected from alkanes having about 5 to 20 carbon atoms, alkyl-substituted benzenes having about 9 to 15 carbon atoms, tetrahydronaphthalene, and decahydronaphthalene comprising the steps of:
   (1) intimately contacting the hydroformylation product solution with an extraction solution comprising methanol, water and 1 to 5000 ppm of an alkali metal salt of a carboxylic acid having 4 to 30 carbon atoms at a temperature of about 20° to 60° C. to form a 2-phase mixture; and (2) separating the mixture of step (1) to obtain:
  (a) a hydroformylation solvent phase containing catalyst components; and
  (b) an methanol/water phase containing the aldehyde; wherein the volume ratio of methanol to water of the extraction solution is about 5:1 to 1:1 and the difference between the densities of the hydroformylation product solution and the extraction solution is at least 0.05 g/mL.

12. Process according to claim 11 wherein the process includes (i) heating the methanol/water of step (2)(b) to vaporize at least 50 weight percent of the methanol and form a liquid phase of the aldehyde and (ii) separating the aldehyde from the liquid phase.

13. Process according to claim 11 wherein the extraction solution comprises methanol, water and about 10 to 1400 ppm of an alkali metal salt of a carboxylic acid having about 8 to 18 carbon atoms and the aldehyde has the general formula:

wherein
  $R^1$ is straight or branched chain alkyl of about 5 to 8 carbon atoms;
  $R^2$ is straight or branched chain alkylene having about 2 to 18 carbon atoms; and
  $R^3$ is hydroxy, alkoxy of up to about 4 carbon atoms, carboxyl or alkoxycarbonyl of 2 to about 10 carbon atoms.

14. Process according to claim 11 wherein the extraction solution comprises methanol, water and about 10 to 1400 ppm of an alkali metal salt of a carboxylic acid having about 8 to 12 carbon atoms and the aldehyde has the general formula

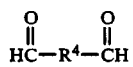

wherein $R^4$ is straight- or branched-chain alkylene having about 5 to 20 carbon atoms.

15. Process according to claim 11 wherein the aldehyde has the general formula

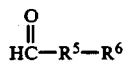

wherein
  $R^5$ is cycloalkylene having about 5 to 12 carbon atoms; and
  $R^6$ is formyl, formylethyl, carboxyl or alkoxycarbonyl of 2 to about 10 carbon atoms.

16. Process for the recovery of an aldehyde product from a hydroformylation product solution comprising (i) a high-boiling aldehyde, (ii) hydroformylation catalyst components comprising rhodium and an organophosphine compound, and (iii) a hydroformylation solvent selected from the group consisting of alkanes having about 5 to 20 carbon atoms, benzene, toluene, xylene isomers, alkyl-substituted benzenes having about 9 to 15 carbon atoms, tetrahydronaphthalene, decahydronaphthalene and dialkyl benzenedicarboxylate esters, by the steps of:
  (1) intimately contacting the hydroformylation product solution with an extraction solution comprising a primary alkanol and water to form a 2-phase mixture;
  (2) separating the mixture of step (1) to obtain:
    (a) a hydroformylation solvent phase containing catalyst components; and
    (b) an alkanol/water phase containing the high-boiling aldehyde;
  (3) intimately contacting the alkanol/water phase of step (2) with an organic solvent selected from hydroformylation solvent, olefin feedstock or a mixture thereof; and
  (4) separating the mixture of step (3) to obtain:
    (a) an organic solvent phase containing catalyst components present in the alkanol/water phase of step (3); and
    (b) an alkanol/water phase containing the high-boiling aldehyde.

17. Process according to claim 16 for the recovery of an aldehyde product from a hydroformylation product solution comprising (i) an aldehyde having a boiling point of at least 125° C., (ii) hydroformylation catalyst components comprising rhodium and an organophosphine compound, and (iii) a hydroformylation solvent selected from alkanes having about 5 to 20 carbon atoms, alkylsubstituted benzenes having about 9 to 15 carbon atoms, tetrahydronaphthalene, and decahydronaphthalene comprising the steps of:
  (1) intimately contacting the hydroformylation product solution with an extraction solution comprising methanol and water at a temperature of about 20 to 60° C. to form a 2-phase mixture; and
  (2) separating the mixture of step (1) to obtain:
    (a) a hydroformylation solvent phase containing catalyst components; and
    (b) a methanol/water phase containing the aldehyde;
  (3) intimately contacting the alkanol/water phase of step (2) with an organic solvent selected from hydroformylation solvent, olefin feedstock or a mixture thereof; and
  (4) separating the mixture of step (3) to obtain:
    (a) an organic solvent phase containing catalyst components present in the alkanol/water phase of step (3); and
    (b) an alkanol/water phase containing the high-boiling aldehyde; wherein the volume ratio of methanol to water of the extraction solution is about 5:1 to 1:1 and the difference between the densities of the hydroformylation product solution and the extraction solution is at least 0.05 g/mL.

18. Process according to claim 17 wherein the process includes (i) heating the methanol/water of step (4)(b) to vaporize at least 50 weight percent of the methanol and form a liquid phase of the aldehyde and
  (ii) separating the aldehyde from the liquid phase.

19. Process for the recovery of an aldehyde product from a hydroformylation product solution comprising (i) a high-boiling aldehyde, (ii) hydroformylation catalyst components comprising rhodium and an organophosphine compound, and (iii) a hydroformylation solvent selected from the group consisting of alkanes having about 5 to 20 carbon atoms, benzene, toluene, xylene isomers, alkyl-substituted benzenes having about 9 to 15 carbon atoms, tetrahydronaphthalene, decahydronaphthalene and dialkyl benzenedicarboxylate esters, and the conversion of the aldehyde to the corresponding alcohol comprising the steps of:

(1) intimately contacting the hydroformylation product solution with an extraction solution comprising a primary alkanol and water to form a 2-phase mixture; and
(2) separating the mixture of step (1) to obtain:
  a hydroformylation solvent phase containing catalyst components; and
  (b) an alkanol/water phase containing the high-boiling aldehyde;
(3) subjecting the alkanol/water phase containing the high boiling aldehyde to catalytic hydrogenation to convert the aldehyde to the corresponding alcohol.

20. Process according to claim 19 for the recovery of an aldehyde product from a hydroformylation product solution comprising (i) an aldehyde having a boiling point of at least 125° C., (ii) hydroformylation catalyst components comprising rhodium and an organophosphine compound, and (iii) a hydroformylation solvent selected from alkanes having about 5 to 20 carbon atoms, alkyl substituted benzenes having about 9 to 15 carbon atoms, tetrahydronaphthalene, and decahydronaphthalene, and the conversion of the aldehyde to the corresponding alcohol comprising the steps of:
(1) intimately contacting the hydroformylation product solution with an extraction solution comprising methanol and water at a temperature of about 20° to 60° C. to form a 2 phase mixture; and
(2) separating the mixture of step (1) to obtain:
  (a) a hydroformylation solvent phase containing catalyst components; and
  (b) a methanol/water phase containing the aldehyde;
(3) subjecting the methanol/water phase containing the high boiling aldehyde to hydrogenation at a temperature of about 25° to 150° C. and a total pressure of about 10 to 1000 psig in the presence of a hydrogenation catalyst;
wherein the volume ratio of methanol to water of the extraction solution is about 5:1 to 1:1 and the difference between the densities of the hydroformylation product solution and the extraction solution is at least 0.05 g/mL.

21. Process according to claim 20 wherein the aldehyde has the general formula:

wherein
R$^1$ is straight or branched chain alkyl of about 5 to 8 carbon atoms;
R$^2$ is straight or branched chain alkylene having about 2 to 18 carbon atoms; and
R$^3$ is hydroxy, alkoxy of up to about 4 carbon atoms, carboxyl or alkoxycarbonyl of 2 to about 10 carbon atoms;
and the hydrogenation is carried out at a temperature of about 100° to 150° C. and about 100 to 500 psig in the presence of a catalytic amount of Raney nickel, molybdenum-promoted nickel, Raney cobalt or copper chromite.

22. Process according to claim 20 wherein the aldehyde has the general formula

wherein R$^4$ is straight or branched chain alkylene having about 5 to 20 carbon atoms; and the hydrogenation is carried out at a temperature of about 100° to 150° C. and about 100 to 500 psig in the presence of a catalytic, amount of Raney nickel, molybdenum promoted nickel, Raney cobalt or copper chromite.

23. Process according to claim 20 wherein the aldehyde has the general formula

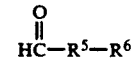

wherein
R$^5$ is cycloalkylene having about 5 to 12 carbon atoms; and
R$^6$ is formyl, formylethyl, carboxyl or alkoxycarbonyl of 2 to about 10 carbon atoms; and the hydrogenation is carried out at a temperature of about 100° to 150° C. and about 100 to 500 psig in the presence of a catalytic amount of Raney nickel, molybdenum-promoted nickel, Raney cobalt or copper chromite.

* * * * *

UNITED STATES PATENT AND TRADEMARK OFFICE
CERTIFICATE OF CORRECTION

PATENT NO. : 5,138,101
DATED : August 11, 1992
INVENTOR(S) : Thomas J. Devon

It is certified that error appears in the above-identified patent and that said Letters Patent is hereby corrected as shown below:

Column 34, line 43 (Claim 1, line 8), after "isomers," ---alkyl—substituted benzenes having about 9 to 15 carbon atoms,--- should be inserted.

Column 36, line 16 (Claim 9, line 6), "form" should be ---from---.

Signed and Sealed this

Seventeenth Day of August, 1993

Attest:

BRUCE LEHMAN

*Attesting Officer*  *Commissioner of Patents and Trademarks*